United States Patent
Yang et al.

(10) Patent No.: US 12,410,398 B2
(45) Date of Patent: Sep. 9, 2025

(54) METHODS OF HUMAN RETINAL PROGENITOR CELL ISOLATION AND CULTURE

(71) Applicant: The Regents of the University of California, Oakland, CA (US)

(72) Inventors: Jing Yang, Irvine, CA (US); Henry Klassen, Irvine, CA (US)

(73) Assignee: The Regents of the University of California, Oakland, CA (US)

( * ) Notice: Subject to any disclaimer, the term of this patent is extended or adjusted under 35 U.S.C. 154(b) by 997 days.

(21) Appl. No.: 17/280,702

(22) PCT Filed: Sep. 27, 2019

(86) PCT No.: PCT/US2019/053520
§ 371 (c)(1),
(2) Date: Mar. 26, 2021

(87) PCT Pub. No.: WO2020/069360
PCT Pub. Date: Apr. 2, 2020

(65) Prior Publication Data
US 2021/0380939 A1    Dec. 9, 2021

Related U.S. Application Data

(60) Provisional application No. 62/737,622, filed on Sep. 27, 2018.

(51) Int. Cl.
| | | |
|---|---|---|
| *C12N 5/079* | (2010.01) |
| *A01N 1/02* | (2006.01) |
| *A01N 1/122* | (2025.01) |
| *A01N 1/162* | (2025.01) |

(52) U.S. Cl.
CPC ........... *C12N 5/0621* (2013.01); *A01N 1/122* (2025.01); *A01N 1/162* (2025.01); *C12N 2509/00* (2013.01); *C12N 2523/00* (2013.01)

(58) Field of Classification Search
None
See application file for complete search history.

(56) References Cited

U.S. PATENT DOCUMENTS

| | | |
|---|---|---|
| 6,045,791 A | 4/2000 | Liu |
| 2009/0238800 A1 | 9/2009 | Lashkari et al. |
| 2016/0319243 A1* | 11/2016 | Klassen ............... C12N 5/0621 |

* cited by examiner

*Primary Examiner* — Nghi V Nguyen
(74) *Attorney, Agent, or Firm* — Gregory P. Einhorn; Greer, Burns & Crain, Ltd.

(57) ABSTRACT

Disclosed herein are compositions and methods for treating, ameliorating or preventing a retinal disease or condition; improving a photopic (day light) vision; for improving correcting visual acuity, improving macular function, improving a visual field, or improving scotopic (night) vision by administration of retinal progenitor cells.

19 Claims, 2 Drawing Sheets

|  | Protocol A | Protocol B-1 | Protocol B-2 | Comments |
|---|---|---|---|---|
| P0 (isolation) | mechanical +T 1min | mechanical only, no T | mechanical only, no T | Protocol B allows live cells to attach to flask.; dead cells are removed on day 2/3 during medium change. This decreases the DNA released by dead cells, thus eliminates a major source of cell loss during harvest and early passaging. |
| P1 | T+P=1:1, 5-7min, 37C | T+E+P=1:1:3, 7-8min, 37C | T+E=1:4, 7-8 min, 37C | adding EDTA to help break up clusters while avoiding trypsin-mediated lysis and accumulation of extracellular DNA. strategy is to gradually reduce the size of clusters but avoid complete dissociation down to single cells during harvest/early passage (tissue to cell transformation) |
| P2 | T+P=1:1, 5-7min, 37C | T+P=1:1, 5-7 min, 37C | T+E+P=1:1:3, 5-6min, 37C | gradually decrease EDTA to avoid potential negative EDTA impact on chromosomes |
| P3 | T+P=1:1, 5-7min, 37C | T+P=1:1, 5-7 min, 37C | T+P=1:1, 5-7 min, 37C | |
| P4 | T+P=1:1, 5-7min, 37C | T+P=1:1, 5-7 min, 37C | T+P=1:1, 5-7 min, 37C | |
| P5 | T+P=1:1, 5-7min, 37C | T+P=1:1, 5-7 min, 37C | T+P=1:1, 5-7 min, 37C | |
| | <= 4hrs | 8-24 hrs | 8-24 hrs | Transportation time |

Legend: T = trypLE; E = EDTA; P = PBS

FIG. 2

METHODS OF HUMAN RETINAL PROGENITOR CELL ISOLATION AND CULTURE

RELATED APPLICATIONS

This application is a national phase application claiming benefit of priority under 35 U.S.C. § 371 to International (PCT) Patent Application serial number PCT/US2019/053520, filed Sep. 27, 2019, which claims the benefit of priority to U.S. provisional patent application Ser. No. 62/737,622, filed on Sep. 27, 2018, the contents of which are incorporated by reference in their entirety.

TECHNICAL FIELD

The subject matter described herein relates generally to the fields of stem cell biology and regenerative medicine. In alternative embodiments, provided herein are methods for isolating primary retinal cells obtained or isolated from a human sample. In alternative embodiments, provided are compositions and methods for treating, ameliorating or preventing a retinal disease or condition; improving a photopic (day light) vision; for improving visual acuity, improving macular function, improving a visual field, or improving scotopic (night) vision by administration of retinal progenitor cells or regenerating a macular and/or a scotopic visual function.

BACKGROUND

Retinal degeneration refers to the deterioration or degeneration caused by the progressive and irreversible decline and death of photoreceptor cells in the retina. The death of photoreceptor cells can result in blindness. Thus, a need exists in the art for effective treatments to restore injured and lost photoreceptor cells and restore visual function.

SUMMARY

The disclosure provides methods of isolating primary retinal cells obtained, or having been obtained, from a human sample by: (a) processing, or having processed, an obtained sample of human retinal tissues from a human of about 12 weeks to about 28 weeks gestational age, (b) mechanically dissociating the obtained sample, (c) determining the viability and quantity of the primary retinal cells obtained from the sample, and (d) confirming, or having confirmed, the morphology of the obtained primary retinal cells to generate a dissociated suspension of cells and cell clusters.

In some embodiments of the methods of the disclosure, the human retinal tissue is obtained from one or a pair of human eyeballs. In some embodiments of the methods of the disclosure, the eyeball(s) possess a normal morphology comprising intact globe(s), clear cornea, and/or normal shape. In some embodiments, the fetal eyeball (containing human retinal tissue) is stored in RPMI-1640 medium with L-glutamine and stored on ice immediately after organ harvest from the donor. In any of these methods, the stored human retinal tissue is delivered and used within a defined period of time following harvest. In various embodiments, the human retinal tissue is shipped on ice and delivered within a transportation window. By way of non-limiting example, the transportation window may be from about 1 to about 26 or more hours (e.g., 1, 1.5, 2, 2.5, 3, 3.5, 4, 4.5, 5, 5.5, 6, 6.5, 7, 7.5, 8, 8.5, 9, 9.5, 10, 10.5, 11, 11.5, 12, 12.5, 13, 13.5, 14, 14.5, 15, 15.5, 16, 16.5, 17, 17.5, 18, 18.5, 19, 19.5, 20, 20.5, 21, 21.5, 22, 22.5, 23, 23.5, 24, 24.5, 25, 25.5, or 26 hours), for example from about 4.5 to about 21.5 hours (e.g., 1, 1.5, 2, 2.5, 3, 3.5, 4, 4.5, 5, 5.5, 6, 6.5, 7, 7.5, 8, 8.5, 9, 9.5, 10, 10.5, 11, 11.5, 12, 12.5, 13, 13.5, 14, 14.5, 15, 15.5, 16, 16.5, 17, 17.5, 18, 18.5, 19, 19.5, 20, 20.5, 21, or 21.5) or from about 7 to about 26 hours (e.g., 7, 7.5, 8, 8.5, 9, 9.5, 10, 10.5, 11, 11.5, 12, 12.5, 13, 13.5, 14, 14.5, 15, 15.5, 16, 16.5, 17, 17.5, 18, 18.5, 19, 19.5, 20, 20.5, 21, 21.5, 22, 22.5, 23, 23.5, 24, 24.5, 25, 25.5, or 26 hours).

In some embodiments of the methods of the disclosure, processing the obtained sample at step (a) comprises: (i) following organ harvest, removing the eyeball(s) from the RPMI-1640 medium and rinsing 1 to 5 times (e.g., 1, 2, 3, 4, or 5 times) with ice cold phosphate buffered saline (PBS) supplemented with antibiotics, (ii) removing an optic nerve and mesenchymal tissue from the eyeball to remove all extra-ocular cells, (iii) washing the eyeball with ice cold PBS supplemented with antibiotics, (iv) puncturing the globe at the limbus using a needle, (v) circumferentially cutting along the limbus with microsurgical scissors, (vi) removing a lens, cornea, and associated vitreous body, (vii) dissociating the retina(s) from the retinal pigment epithelium (RPE) layer to produce isolated retinas, (viii) placing the isolated retina(s) in a Petri-dish containing ice cold medium or PBS supplemented with antibiotic.

In some embodiments of the methods of the disclosure, mechanically dissociating at step (b) comprises mechanically dissociating the retina(s) obtained in step (a) by: (i) transferring the retina(s) to a conical tube, (ii) mechanically dissociating the retina(s) to produce dissociated retinas, (iii) washing the Petri-dish with a serum-free medium supplemented with an antibiotic and transferring medium containing any residual dissociated retinas to the conical tube containing the dissociated retina(s), (iv) pelleting the dissociated retina(s) via centrifugation, and (v) removing the supernatant. In some embodiments, the mechanical dissociation of the retina is performed via trituration with a sterile pipet. In some embodiments, the dissociated retina is pelleted via centrifugation at about 10 to about 1000×g for period between about 0 and about 30 minutes at 1 to 50° C.

In some embodiments of the methods of the disclosure, step determining the viability and quantity of the primary retinal cells at (c) comprises: (i) resuspending the pelleted retinal tissue from step (b) in ice cold antibiotic-supplemented serum-free medium, (ii) determining the quantity and viability of retinal cells and retinal cell clusters obtained from the mechanical dissociation of the retinal tissue, (iii) seeding the cells into fibronectin-coated cell culture flasks or plates containing antibiotic-supplemented serum-free medium, (iv) incubating the retinal cell containing flasks or plates at 10 to 50° C. In some embodiments, the quantity and viability of cells are measured by an NC-200 cell counter. In some embodiments, the counted number of cells is between about 1 and about 1,000,000,000 cells. In some embodiments, the percentage of viable counted cells is between about 10 and about 100. In some embodiments, the flasks or plates are seeded with between about 1 and about 1,000,000,000 cells. In some embodiments, the incubation of retinal cell containing flasks or plates is at 37° C. under 0 to 30% $CO_2$ and 0 to 50% $O_2$.

In some embodiments of the methods of the disclosure, step (d) comprises confirming that retinal cells seeded into cell culture flasks or plates consist of retinal cell clusters comprised of about 1 to about 100 cells.

In some embodiments of the methods of the disclosure, the antibiotic used to supplement PBS or serum-free medium is Gentamycin. In some embodiments, the antibiotic is used at a concentration of about 0 to about 10,000 µg/mL.

The disclosure provides methods of isolating primary retinal cells from a human sample comprising: (a) isolating a retinal sample comprising a plurality of primary retinal cells from the human sample, wherein the human sample is from a human donor of about 12 weeks to about 28 weeks gestational age, (b) mechanically dissociating the plurality of primary retinal cells in the retinal sample isolated in step (a) without digesting the plurality of primary retinal cells with a protease, thereby generating a dissociated suspension of cells and cell clusters, and (c) determining the viability, quantity, and morphology of the primary retinal cells from the retinal sample, wherein at least $30 \times 10^6$ viable primary retinal cells are produced.

In some embodiments of the methods of the disclosure, the human sample is one or a pair of human eyeballs. In some embodiments, the eyeball(s) possess a normal morphology comprising intact globe(s), clear cornea, normal shape, or any combination thereof. In some embodiments, the human sample is placed in a transport cell culture medium after harvest from the human donor prior to step (a). In some embodiments, the transport cell culture medium comprises RPMI-1640 with L-glutamine or Advanced DMEM/F12. In some embodiments, the transport cell culture medium comprises Gentamicin at about 0.5 to 50 micrograms per milliliter (mL), optionally the transport cell culture medium comprises about 50 micrograms per milliliter Gentamicin. In some embodiments, the human sample is stored at about 1 to 8° C. immediately after placement in the transport cell culture medium, for example by placement on ice.

In some embodiments of the methods of the disclosure, the human sample is used within about 7 to about 26 hours following harvest from the human donor.

In some embodiments of the methods of the disclosure, isolating the retinal sample from the human sample at step (a) comprises: (i) removing the one or pair of human eyeballs from the transport culture medium, (ii) rinsing the one or pair of human eyeballs with about 1-8° C. phosphate buffered saline (PBS) supplemented with antibiotic, (iii) removing an optic nerve and mesenchymal tissue from the one or a pair of human eyeballs, (iv) washing the one or pair of human eyeballs with about 1-8° C. PBS supplemented with an antibiotic, (v) puncturing a globe of each of the one or pair of human eyeballs at the limbus using a needle, (vi) circumferentially cutting along a limbus of the one or pair of human eyeballs, (vii) removing a lens, cornea, and associated vitreous body from the one or pair of human eyeballs, (viii) dissociating the retina(s) from the retinal pigment epithelium (RPE) layer to produce an isolated retina or pair of isolated retinas, and (ix) placing the isolated retina or pair of isolated retinas in about 1-8° C. culture medium or PBS, wherein the culture medium or PBS is supplemented with an antibiotic. In some embodiments, step (ii) is repeated 1-5 times, or 3 times. In some embodiments, step (iii) removes some or all extra-ocular cells.

In some embodiments of the methods of the disclosure, mechanically dissociating the plurality of primary retinal cells at step (b) comprises: (i) transferring the retinal sample to a tube, (ii) mechanically dissociating the retinal sample to produce a plurality of dissociated primary retinal cells, (iii) pelleting the plurality of dissociated primary retinal cells via centrifugation, and (iv) removing the supernatant. In some embodiments, the mechanical dissociation of the retina is performed via trituration with a sterile pipet. In some embodiments, the trituration is performed between 2 and 50 times, between 2 and 10 times, or between 4 and 8 times. In some embodiments, the plurality of dissociated primary retinal cells is pelleted via centrifugation at about 140×g for a period of about 3 minutes at 4° C. In some embodiments, the methods comprise washing the plurality of dissociated primary retinal cells with culture medium or PBS supplemented with an antibiotic after step (ii) and before step (iii).

In some embodiments of the methods of the disclosure, the plurality of dissociated primary retinal cells comprises single cells and clusters of cells.

In some embodiments of the methods of the disclosure, determining the viability, quantity, and morphology of the primary retinal cells at step (c) comprises: (i) resuspending the pelleted primary retinal cells from step (b) in about 1-8° C. antibiotic-supplemented culture medium, (ii) seeding the plurality of dissociated retinal cells into one or more coated cell culture flasks or plates containing culture medium, optionally wherein the cell culture medium is supplemented with an antibiotic, (iii) incubating the plurality of dissociated retinal cells at 10 to 50° C., optionally wherein the incubation occurs at 37° C., and (iv) determining the quantity and viability of primary retinal cells and retinal cell clusters. In some embodiments, the quantity and viability of primary retinal cells are measured by an NC-200 cell counter using an aggregate cell counting method, a Hemocytometer or Trypan Blue. In some embodiments, the number of viable primary retinal cells is between about $20 \times 10^6$ and about $1 \times 10^9$ viable primary retinal cells, or between about 73-147× $10^6$ viable primary retinal cells. In some embodiments, the percentage of viable counted cells is between about 10% and about 100%, or between about 68% and about 85%.

In some embodiments of the methods of the disclosure, the flasks or plates are seeded at step (ii) with between about 1 and about 1,000,000,000 cells.

In some embodiments of the methods of the disclosure, the plurality of dissociated retinal cells are incubated at: (1) about 37° C. under 0 to 30% $CO_2$ and 0 to 50% $O_2$; (2) about 37° C., less than or equal to 5% $CO_2$ and less than or equal to 20% $O_2$; or (3) about 37° C., less than or equal to 5% $CO_2$ and less than or equal to 3% $O_2$. In some embodiments, the plurality of dissociated retinal cells are incubated at 37° C., less than or equal to 5% $CO_2$ and less than or equal to 3% $O_2$.

In some embodiments of the methods of the disclosure, determining the viability, quantity, and morphology of the primary retinal cells at step (c) comprises (i) visually inspecting the plurality of dissociated retinal cells under a microscope, and (ii) confirming that a plurality of the retinal cells seeded into cell culture flasks or plates comprise clusters of retinal cell clusters that consist of about 2 to about 1000 cells.

In some embodiments of the methods of the disclosure, serum-free medium comprises: (a) Advanced DMEM/F12, (b) N-2 supplement, (c) EGF (recombinant human epidermal growth factor), (d) bFGF (basic fibroblast growth factor), and/or (e) GlutaMAX I.

In some embodiments of the methods of the disclosure, the culture medium is serum free. In some embodiments, the culture medium comprises a complete medium. In some embodiments, the medium comprises Dulbecco's Modified Eagle Medium DMEM/F12, Advanced DMEM/F12, Knockout DMEM/F12, Neurobasal media, ReNcell or Ultraculture media. In some embodiments, the culture medium comprises Advanced DMEM/F12. In some embodiments the culture medium comprises N-2 Supplement and GlutaMAX-I. In some embodiments the culture medium comprises B27, B27 xeno-free, or Stempro. In some embodiments the culture medium comprises supplements or additives that support cell survival or growth. In some embodiments, the supplements or additives that support cell survival or growth are selected from the group consisting of L-glutamine, recombinant human epidermal growth factor (EGF), basic fibroblast growth factor (bFGF), other growth factors, and a combination thereof. In some embodiments, the antibiotic comprises Gentamicin at a concentration of about 0.5 to about 50 µg/mL, optionally wherein the concentration of Gentamicin is about 30 µg/mL.

The disclosure provides a method of culturing isolated primary human retinal cells to produce a population of non-immortal human retinal progenitor cells comprising: (a) culturing a suspension of isolated primary retinal cells in serum-free media in culture flasks or plates coated with a xeno-free fibronectin, an ornithine, a polylysine, or a laminin at standard oxygen levels for between about 4 and 6 passages, (b) subsequently culturing the suspension in serum-free media at low oxygen levels for between about an additional 3 and 6 passages, wherein the cells are passaged at between 40% to 90% confluence and treated with an enzyme at each passage to dissociate the cells and adding fresh culture media, and (c) subsequently cryopreserving the cells, thereby making a population of non-immortal human retinal progenitor cells.

In some embodiments of the methods of the disclosure, following the subsequent culturing of the suspension at low oxygen levels, the cells are allowed to grow without passaging for a period of time at standard oxygen levels. In some embodiments, the period of time between passages is 3 to 5 days (e.g., 3, 4, or 5 days).

In some embodiments of the methods of the disclosure, the enzymatic solution used to dissociate cells comprises trypsin or equivalent. In some embodiments, the cells are dissociated at the first passage using an enzymatic solution comprising trypsin or equivalent, and EDTA at about a 1:4 ratio. In some embodiments, the trypsin or equivalent and EDTA are at a ratio of about 1:3, 1:3.1, 1:3.2, 1:3.3, 1:3.4, 1:3.5, 1:3.6, 1:3.7, 1:3.8, 1:3.9, 1:4.0, 1:4.1, 1:4.2, 1:4.3, 1:4.4, 1:4.5, 1:4.6, 1:4.7, 1:4.8, 1:4.9 or 1:5.0 at the first passage. In some embodiments, the cells are dissociated at the first passage using an enzymatic solution comprising trypsin or equivalent, EDTA and DPBS at about a 1:1:3 ratio. In some embodiments, the trypsin or equivalent, EDTA and DPBS are at a ratio of about 1:1:2, 1:1:2.1, 1:1:2.2, 1:1:2.3, 1:1:2.4, 1:1:2.5, 1:1:2.6, 1:1:2.7, 1:1:2.8, 1:1:2.9, 1:1:3.0, 1:1:3.1, 1:1:3.2, 1:1:3.3, 1:1:3.4, 1:1:3.5, 1:1:3.6, 1:1:3.7, 1:1:3.8, 1:1:3.9 or 1:1:4.0 at the first passage. In some embodiments, the cells are dissociated at the first passage for between 6-10 minutes at about 37° C. In some embodiments, the cells are dissociated at the second passage using an enzymatic solution comprising trypsin or equivalent, EDTA and DPBS at about a 1:1:3 ratio. In some embodiments, the trypsin or equivalent, EDTA and DPBS are at a ratio of about 1:1:2, 1:1:2.1, 1:1:2.2, 1:1:2.3, 1:1:2.4, 1:1:2.5, 1:1:2.6, 1:1:2.7, 1:1:2.8, 1:1:2.9, 1:1:3.0, 1:1:3.1, 1:1:3.2, 1:1:3.3, 1:1:3.4, 1:1:3.5, 1:1:3.6, 1:1:3.7, 1:1:3.8, 1:1:3.9 or 1:1:4.0 at the second passage. In some embodiments, the cells are dissociated at the second passage using an enzymatic solution comprising trypsin or equivalent, and EDTA, at a ratio of about 1:1. In some embodiments, the trypsin or equivalent and EDTA are at a ratio of about 1:0.5, 1:0.6, 1:0.7, 1:0.8, 1:0.9, 1:1, 1:1.1, 1:1.2, 1:1.3, 1:1.4, or 1:1.5 at the second passage. In some embodiments, the cells are dissociated at the second passage for between 4 to 8 minutes at about 37° C. In some embodiments, the cells are dissociated at the third passage and all further passages using an enzymatic solution comprising trypsin or equivalent, and EDTA, at a ratio of about 1:1. In some embodiments, the trypsin or equivalent and EDTA are at a ratio of about 1:0.5, 1:0.6, 1:0.7, 1:0.8, 1:0.9, 1:1, 1:1.1, 1:1.2, 1:1.3, 1:1.4, or 1:1.5 at the third and all further passages. In some embodiments, the cells are dissociated at the third and all further passages for between 4 to 8 minutes at 37° C. In some embodiments, the trypsin or equivalent comprises TrypLE, for example TrypLE Express or TrypLE Select. In some embodiments, the dissociation is halted by addition an excess of DMEM or PBS. In some embodiments, cell count and viability is determined following dissociation. In some embodiments, the cell count and viability are determined via NC-200 cell counter.

The disclosure provides methods culturing isolated primary human retinal cells to produce a population of non-immortal human retinal progenitor cells, the methods comprising: (a) seeding one or more coated culture flasks or plates containing culture media at a first passage with a plurality of primary retinal cells produced by the method described herein to produce a plurality of cultured retinal cells; (b) seeding one or more coated culture flasks or plates containing culture medium at a second passage with a plurality of cultured retinal cells produced by the first passage; (c) seeding one or more coated culture flasks or plates containing culture medium at a third with a plurality of cultured retinal cells produced by the second passage; and (d) cryopreserving the plurality of cultured retinal cells, wherein the one or more coated culture flasks or plates are seeded at a density of about $1 \times 10^4$ cells per square centimeter ($cm^2$) to about $2 \times 10^6$ cells/$cm^2$, the seeding density at the first passage is greater than the seeding density at the second passage, and the seeding density at the second passage is greater than the seeding density at the third passage, thereby producing the population of non-immortal human retinal progenitor cells.

In some embodiments of the methods of the disclosure, the methods further comprises seeding one or more coated culture flasks or plates containing culture medium at one or more further passages with a plurality of cultured retinal cells produced by an immediately prior passage In some embodiments of the methods of the disclosure, the culture flasks or plates are coated with xeno free fibronectin, ornithine, poly-lysine, laminin, or a combination thereof.

In some embodiments of the methods of the disclosure, the plurality of primary or cultured retinal cells are cultured at: (1) about 37° C. under 0 to 30% $CO_2$ and 0 to 50% $O_2$, (2) about 37° C., less than or equal to 5% $CO_2$ and less than or equal to 20% $O_2$; or (3) about 37° C., less than or equal to 5% $CO_2$ and less than or equal to 3% $O_2$. In some embodiments, the plurality of primary or cultured retinal cells are cultured at about 37° C., less than or equal to 5% $CO_2$ and less than or equal to 3% $O_2$. In some embodiments, the period of time between two immediately sequential passages is 2 to 8 days, 3 to 6 days, 4 to 5 days, or 3 to 4 days. In some embodiments, the period of time between two immediately sequential passages is 3 to 4 days.

In some embodiments of the methods of the disclosure, the plurality of primary retinal cells are dissociated at the first passage with a first enzymatic solution comprising: (1) trypsin or equivalent, and Ethylenediamine tetraacetic acid (EDTA), or (2) trypsin or equivalent, EDTA, and DPBS. In some embodiments, wherein the trypsin equivalent is TrypLE. In some embodiments, (1) the TrypLE and EDTA are at a ratio of 1:4 in the first enzymatic solution, or (2) the TrypLE, the EDTA and the DPBS are at a ratio of 1:1:3. In some embodiments, the plurality of primary retinal cells are dissociated for between about 5-20 minutes, about 6-10 minutes, or between about 7-8 minutes, at about 37° C. In some embodiments, the plurality of primary retinal cells between about 7-8 minutes, at about 37° C.

In some embodiments of the methods of the disclosure, the plurality of cultured retinal cells are dissociated at the second passage with a second enzymatic solution comprising: (1) trypsin or equivalent, EDTA and DPBS, or (2) trypsin or equivalent, and DPBS. In some embodiments, the trypsin equivalent is TrypLE. In some embodiments, (1) the TrypLE, EDTA, and DPBS at a 1:1:3 ratio in the second enzymatic solution, or (2) the TrypLE and DPBS are at a ratio of 1:1 in the second enzymatic solution. In some embodiments, the plurality of cultured retinal cells are dissociated for between about 5-20 minutes, about 6-10 minutes, or about 7-8 minutes, at about 37° C. In some embodiments, the plurality of cultured retinal cells are dissociated for between about 5-6 minutes, at about 37° C.

In some embodiments of the methods of the disclosure, the plurality of cultured retinal cells are dissociated at the at least third or further passage with a third enzymatic solution comprising trypsin or equivalent, and DPBS. In some embodiments, the trypsin equivalent comprises TrypLE. In some embodiments, the TrypLE and the DPBS are at a ratio of 1:1 in the third enzymatic solution. In some embodiments, the plurality of cultured retinal cells are dissociated for between about 5-10 minutes or about 5 to 7 minutes at about 37° C. at the at least third or further passage. In some embodiments, the at least third or further passage comprises 3 to 5 passages.

In some embodiments of the methods of the disclosure, the methods comprise determining cell count and viability following dissociation of the plurality of cultured retinal cells after the second passage. In some embodiments, at least 50%, at least 60%, at least 70%, at least 80% or at least 90% of the cells are viable.

In some embodiments of the methods of the disclosure, the c cells are seeded in culture flasks or plates at a density of about $0.5 \times 10^6$ to about $3.0 \times 10^6$ cells/cm$^2$ at the first passage, about $0.1 \times 10^6$ to about $0.5 \times 10^6$ cells/cm$^2$ at the second passage, about $0.03 \times 10^6$ to about $0.2 \times 10^6$ cells/cm2 at the third passage, and about 10,000 to about 60,000 cells/cm2 at a fourth and further passages.

The disclosure provides methods of cryopreserving retinal progenitor cells produced using the methods of the disclosure, comprising: (i) enzymatically dissociating the cells using trypsin, (ii) halting the dissociation with an excess of the culture medium or Advanced DMEM/F12, (iii) centrifuging the cells via centrifugation at between 10×g and 10,000×g for 1 to 30 minutes, (iv) resuspending the cells in culture medium and determining the total cell count and viability, (v) adding cryopreservation medium to achieve a final dimethylsulfoxide (DMSO) concentration of between 5 and 30%, (vi) aliquoting a plurality of cells into each cryovial, (vii) freezing each vial by using a Control Rate Freezer, and (viii) placing each vial of cells in liquid $N_2$.

In some embodiments of the methods of the disclosure, the cryopreservation of step is performed by: (a) enzymatically dissociating the cells using 1:1 trypsin or equivalent, and DPBS, (b) halting the dissociation with an excess of DMEM or PBS, (c) pelleting the cells via centrifugation at between 10 and 10,000 g for 1 to 30 minutes, (d) resuspending the cells in serum-free medium and determining the total cell count and viability, (e) adding cryopreservation medium to achieve a final DMSO concentration of between 5 and 30%, (f) aliquoting 0.2 to $100 \times 10^6$ cells into each cryovial, (g) freezing each vial at −80° C. for 6 to 72 hours, and (h) placing each vial of cells in liquid $N_2$.

In some embodiments of the methods of cryopreservation of the disclosure, the trypsin equivalent at step (i) comprises TrypLE. In some embodiments, the cryopreservation medium comprises culture medium and 10% DMSO. In some embodiments, the plurality of cells at step (vi) is about $0.5 \times 10^6$ to $50 \times 10^6$ cells per cryovial, or between about $0.5 \times 10^6$ to about $20 \times 10^6$ cells per mL of culture medium and DMSO.

In some embodiments of the methods of the disclosure, the cells and/or cell clusters are cultured together with supplements or additives that support cell survival or growth. In some embodiments, the supplements or additives that support cell survival or growth are selected from the group consisting of L-glutamine, human recombinant growth factors consisting of EGF and bFGF (Invitrogen), and other growth factors.

In alternative embodiments, provided are pharmaceutical compositions comprising a retinal progenitor cell, or a population or plurality of non-immortal human retinal progenitor cells, isolated by a method of any of the preceding claims, and optionally also comprising a pharmaceutically acceptable excipient.

In alternative embodiments, provided herein are kits comprising a retinal progenitor cell, or a population or plurality of non-immortal human retinal progenitor cells, isolated by a method of any of the preceding claims.

In alternative embodiments, provided are methods for: treating, ameliorating or preventing a retinal disease or condition, improving a photopic (day light) vision, improving correcting visual acuity, improving macular function, improving a visual field, or improving scotopic (night) vision, the methods comprising: (a) administering or having administered to an individual in need thereof a retinal progenitor cell, or a population or plurality of non-immortal human retinal progenitor cells, isolated by a method of any of the preceding claims; or (b) (i) providing or having provided a retinal progenitor cell, or a population or plurality of non-immortal human retinal progenitor cells, isolated by a method of any of the preceding claims; and (ii) administering or having administered the retinal progenitor cell, or the population or plurality or of non-immortal human retinal progenitor cells to an individual in need thereof.

In alternative embodiments, provided are uses of a retinal progenitor cell, or a population or plurality of non-immortal human retinal progenitor cells, isolated by a method of any of the preceding claims, in the manufacture of a medicament for: treating, ameliorating or preventing a retinal disease or condition, improving a photopic (day light) vision, improving correcting visual acuity, improving macular function, improving a visual field, or improving scotopic (night) vision.

In alternative embodiments, provided are retinal progenitor cells, or a population or plurality of non-immortal human retinal progenitor cells, isolated by a method of any of the preceding claims for use in: treating, ameliorating or preventing a retinal disease or condition, improving a photopic (day light) vision, improving correcting visual acuity, improving macular function, improving a visual field, or improving scotopic (night) vision.

Any of the above aspects can be combined with any other aspect of the present disclosure.

BRIEF DESCRIPTION OF THE DRAWINGS

FIG. 2 is a table describing experimental conditions and passage conditions using Protocol B and comparing them to the previous culture method (Protocol A). P means passage number; d means day number; T means TrypLE Select (Invitrogen); E means EDTA (Invitrogen); P means Dulbecco's Phosphate Buffered Saline, or DPBS (Invitrogen).

DETAILED DESCRIPTION

Figure 1:
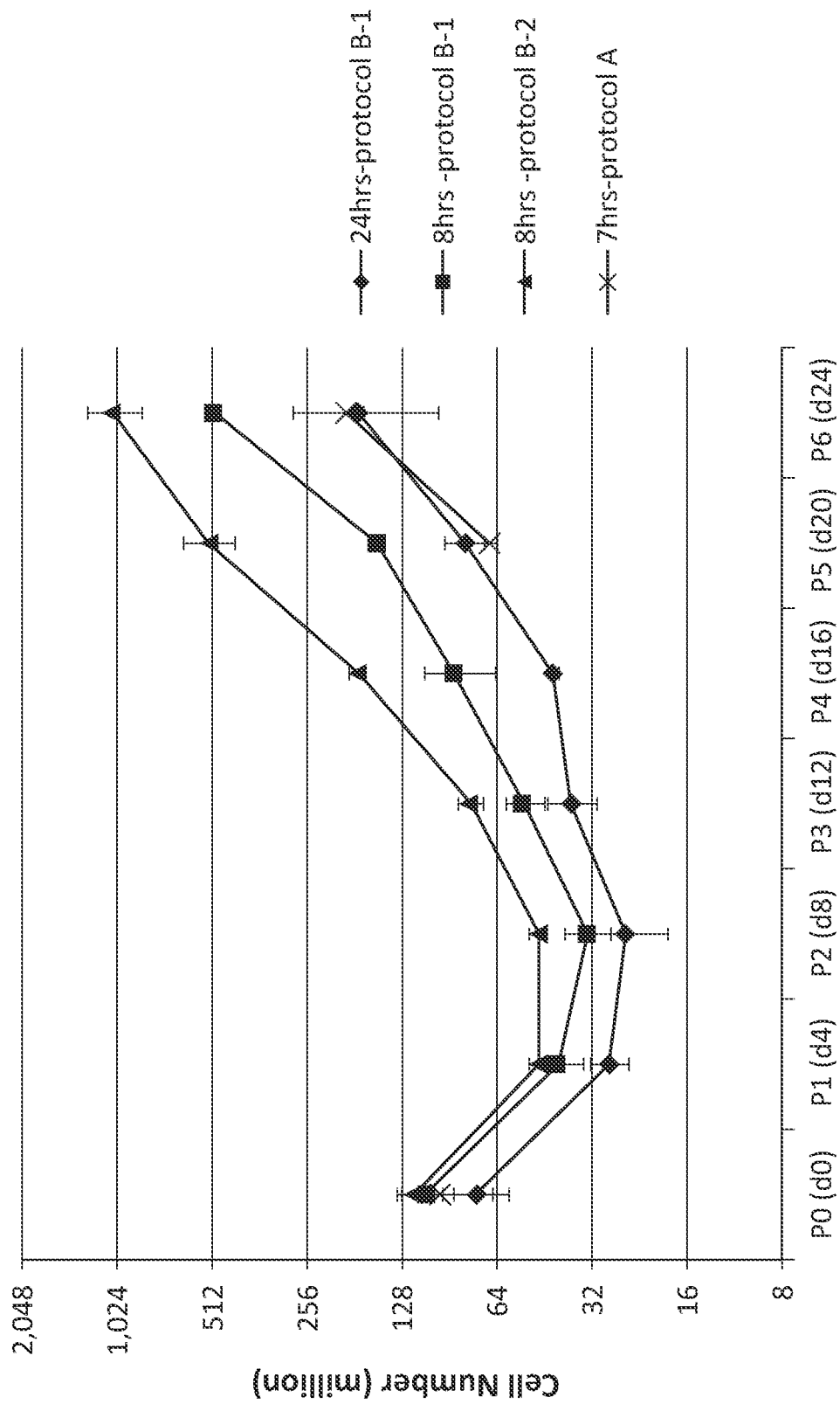
FIG. 1 is a line graph depicting the average number of retina progenitor cells at each passage number. Retinal progenitor cells were isolated from eyeball samples using either Protocol A or Protocol B and were either processed on the same day (7 hours, 8 hours) or after overnight shipping (24 hrs). P means passage number; d means day number. The data points represent the theoretical calculation of the average number of all retina progenitor cells isolated using the same Protocol and cultured under the same conditions.

When fetal eyeballs (and associated retinal tissue) are transported on ice over long distances, the time in transit can be very substantial. During that time the retinal tissue becomes progressively more friable and the potential viability of the constituent cells gradually diminishes. This poses a challenge for cell manufacturing when tissue must be sourced at a distance, since final product yield (over any set time in culture) is impacted by the number of viable cells obtained per retina. However, it is possible to take advantage of the increased tissue friability and eliminate certain steps otherwise utilized to isolate retinal cells. In particular, the use of trypsin to break up the retinal tissue can be eliminated, since the tissue can be broken up with gentle trituration alone. This is easier to perform and shortens the time from tissue to incubator. In addition, the use of EDTA during early passaging also decreases the stress on the cells during this critical period as they recover in culture. By breaking the retina into progressively smaller chunks over successive passages and not attempting to dissociate into single cells until later in the process, viability is further enhanced and the process made less risky to perform. As cellular viability improves, trypsin can be systematically introduced into the passaging process without a negative impact on yield.

In particular, expected cell yields can be adversely impacted when the starting tissue is subjected to substantially longer transportation times than were the case previously. While the changes in the tissue may be difficult to address directly, the isolation and early cell culture protocol can be modified to eliminate sources of cell loss and thereby enhance final yield.

The methods of isolating retinal cells described herein have multiple benefits over previous methods when there is a long time interval between tissue procurement and initiating tissue culture. The methods described herein have benefits that include, but are not limited to, (1) improved yield, (2) ease to perform since the enzymatic step is removed, (3) lower risk of cell lysis and extrusion of DNA with associated cell loss, (4) faster process from tissue isolation to incubator, and (5) enhanced cell viability during early passaging.

Definitions

To facilitate the understanding of this disclosure, a number of terms are defined below. The terminology herein is used to describe specific embodiments of the subject matter described herein, but their usage does not delimit the subject matter, except as outlined in the claims.

Any of the aspects and embodiments described herein can be combined with any other aspect or embodiment as disclosed herein.

Unless defined otherwise, all technical and scientific terms used herein have the same meaning as commonly understood by one of ordinary skill in the art to which the invention pertains. Although other probes, compositions, methods, and kits similar, or equivalent, to those described herein can be used in the practice of the present disclosure, the exemplary materials and methods are described herein. It is to be understood that the terminology used herein is for the purpose of describing particular aspects only, and is not intended to be limiting.

In this disclosure, "comprises," "comprising," "containing," "having," and the like can have the meaning ascribed to them in U.S. Patent law and can mean "includes," "including," and the like; the terms "consisting essentially of" or "consists essentially" likewise have the meaning ascribed in U.S. Patent law and these terms are open-ended, allowing for the presence of more than that which is recited so long as basic or novel characteristics of that which is recited are not changed by the presence of more than that which is recited, but excludes prior art embodiments.

Unless specifically stated or obvious from context, as used herein, the terms "a," "an," and "the" are understood to be singular or plural.

Unless specifically stated or obvious from context, as used herein, the term "or" is understood to be inclusive.

As used herein in other contexts, the term "about," unless indicated otherwise, refers to the recited value, e.g., amount, dose, temperature, time, percentage, etc., +/−10%, +/−9%, +/−8%, +/−7%, +/−6%, +/−5%, +/−4%, +/−3%, +/−2%, or +/−1%.

As used herein, the terms "patient" or "subject" and the like are used interchangeably herein to refer to any mammal, including humans, domestic and farm animals, and zoo, sports, and pet animals, such as dogs, horses, cats, and agricultural use animals including cattle, sheep, pigs, and goats. One exemplary mammal is a human, including adults, children, and the elderly. A subject may also be a pet animal, including dogs, cats and horses. Exemplary agricultural animals comprise cattle and goats.

The terms "treat", "treating", "treatment" and the like, as used herein, unless otherwise indicated, refers to curing, reversing, attenuating, alleviating, minimizing, inhibiting the process of, suppressing, halting, and/or preventing the disease, disorder or condition to which such term applies, or one or more (i.e., not necessarily all) symptoms of such disease, disorder or condition, and includes the administration of any of the compositions, pharmaceutical compositions, or dosage forms described herein, to prevent the onset of the symptoms or the complications, alleviating the symptoms or the complications, attenuating the progression of, and/or eliminating the disease, condition, or disorder. In alternative embodiments, treatment is curative or ameliorating.

As used herein, "preventing" or "prophylaxis" means preventing in whole or in part, or ameliorating or controlling, or reducing or halting the production or occurrence of the thing or event, for example, the disease, disorder or condition, to be prevented.

As used herein, the terms "purified" or "enriched" or the like indicates that the cells or cell populations are removed from their normal tissue environment and are present at a higher concentration as compared to the normal tissue environment. Accordingly, a "purified" or "enriched" cell population may further include cell types in addition to retinal progenitor cells and may include additional tissue components, and the term "purified" or "enriched" does not necessarily indicate the presence of only progenitor cells or exclude the presence of other cell types.

In some embodiments, the retinal progenitor cell populations as disclosed herein may be at least 5% pure, at least 10% pure, at least 15% pure, at least 20% pure, least 25% pure, at least 30% pure, at least 35% pure, at least 40% pure, at least 45% pure, at least 50% pure, at least 55% pure, at least 60% pure, at least 65% pure, at least 70% pure, at least 75% pure, at least 80% pure, at least 85% pure, at least 90% pure, at least 95% pure, at least 96% pure, at least 97% pure, at least 98% pure, at least 99% pure or at any increment between 5% and 99% pure (e.g., 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% retinal progenitor cells).

A "marker" refers to any molecule that can be observed or detected. For example, a marker can include, but is not limited to, a nucleic acid, such as a transcript of a specific gene, a polypeptide product of a gene, a non-gene product polypeptide, a glycoprotein, a carbohydrate, a glycolipid, a lipid, a lipoprotein or a small molecule (for example, molecules having a molecular weight of less than 10,000 Daltons). In alternative embodiments, retinal progenitor cells may be characterized by the presence of one or more markers that can be expressed on the surface of the cells within the cell population (a "cell surface marker"), inside cells within the cell population (i.e., in the nucleus or cytoplasm of a cell), and/or expressed at the RNA or protein level as a "genetic" marker.

The terms "express" and "expression" as used herein refers to transcription and/or translation of a nucleic acid sequence within a host cell. The level of expression of a desired product/protein of interest, for example a marker, in a host cell may be determined or "screened" on the basis of either the amount of corresponding mRNA that is present in the cell, or the amount of the desired polypeptide/protein of interest encoded by the selected sequence as in the present examples. For example, mRNA transcribed from a selected sequence can be quantified or detected by Northern blot hybridization, ribonuclease RNA protection, in situ hybridization to cellular RNA, microarray analysis, or by reverse-transcription polymerase chain reaction (RT-PCR). Proteins encoded by a selected sequence can be detected or quantified by various antibody-based methods, e.g. by ELISA, by Western blotting, by radioimmunoassays, by immunoprecipitation, by assaying for the biological activity of the protein, by immunostaining of the protein (including, e.g., immunohistochemistry and immunocytochemistry), by flow cytometry or fluorescence activated cell sorting ("FACS") analysis, or by homogeneous time-resolved fluorescence (HTRF) assays.

Retinal Progenitor Cells (RPCs)

The isolation, characterization, and use of mammalian retinal progenitor cells is described in detail in WO 2012/158910, the contents of which are herein incorporated by reference in their entirety.

In vertebrate embryonic development, the retina and the optic nerve originate as outgrowths of the developing brain, so that the retina is considered part of the central nervous system (CNS) and is actually brain tissue. The retina is a layered structure with several layers of neurons interconnected by synapses. From closest to farthest from the vitreous body, i.e., from closest to the front exterior of the head towards the interior and back of the head, the retinal layers include: (1) the inner limiting membrane, including Muller cell footplates, (2) the nerve fiber layer containing axons of the ganglion cell nuclei, (3) the ganglion cell layer, which contains nuclei of ganglion cells, and the axons of which become the optic nerve fiber, (4) the inner plexiform layer that contains synapses between the bipolar cell axons and the dendrites of the ganglion and amacrine cells, (5) the inner nuclear layer, which contains the nuclei and surrounding cell bodies (perikarya) of the bipolar cells, (6) the outer plexiform layer, containing projections of rods and cones ending in the rod spherule and cone pedicle, respectively, (7) the outer nuclear layer, which contain cell bodies of rods and cones, (8) the external limiting membrane, which separates the inner segment portions of the photoreceptors from their cell nucleus, (9) the photoreceptor layer, and (10) the retinal pigment epithelium (RPE), which is a single layer of cuboidal cells. The neurons that are directly sensitive to light are the photoreceptor cells, comprised mainly of two types: rods and cones. Rods function mainly in dim light and provide black-and-white vision, while cones support daytime vision and the perception of color. A third type of photoreceptor, the photosensitive ganglion cell, is important for reflexive responses to bright daylight.

Donor fetal retinal cells (e.g., the retinal progenitor cells described herein) can provide a trophic influence for the host retina, notably including host cones. This trophic effect is not only neuroprotective but also has a rapid revitalizing effect on residual host retinal cells as determined by improved visual function. Donor cells are capable of integrating into the retina and, via cellular differentiation, replace photoreceptors (which can be in limited numbers). The overall effect is to both rapidly and sustainably restore and preserve clinically significant degrees of visual function in a retina otherwise destined to fail completely, leaving the patient completely blind. Accordingly, any of the compositions and methods described herein can be used to rapidly and sustainably restore and preserve clinically significant degrees of visual function in a retina in a mammal, e.g., a human. For example, any of the compositions and methods described herein can provide clinically significant trophic influences to a diseased retina, or provide regenerative influences to a macular and/or a scotopic visual function.

The cells in the compositions and populations described herein are a population of closely related cells, rather than an isolated single cell type.

While these cells are not stem cells per se (because they do not meet the definition for true stem cells), they are immature and/or plastic. However, these cells cannot (in the absence of additional manipulation) give rise to a germ layer and/or cannot (in the absence of additional manipulation) give rise to all three (3) germ layers.

Additionally, these cells are pre-specified to make retinal tissue or cells. Thus, these cells may express progenitor markers and retinal markers.

Retinal progenitor cells are not pluripotent and can appear to be multipotent. However, because the cells have never been cultured in a pluripotent state, they are, therefore, safer. While, in some embodiments, mammalian fetal retinal cells or RPC cells can be derived artificially from pluripotent cell lines, they optionally contain no population of residual pluripotent cell types.

The cells described herein are retinal progenitor cells (RPCs), which can be distinguished from a neural progenitor and/or neural stem cells (NSCs). Specifically, such mammalian fetal retinal or RPC cells are multipotent but are not equivalent to NSCs. For example, mammalian fetal retinal or RPC cells are not from the brain, but are from the retina. Additionally, mammalian fetal retinal or RPC cells give rise to photoreceptors, whereas brain-derived progenitors are poor at giving rise to photoreceptors. Likewise, unlike NSCs, mammalian fetal retinal or RPC cells are multipotent but do not (in the absence of additional manipulation) give rise to oligodendrocytes. For example, the mammalian fetal retinal cells or RPC cells give rise to (differentiate into) retinal cells including photoreceptors but not to oligodendrocytes.

Mammalian fetal retinal or RPC cells are obtained (or are obtainable) from a mammalian fetal neural retina, not from a ciliary margin, ciliary epithelium, or RPE. Additionally, mammalian fetal retinal or RPC cells are not descended from differentiated Mueller glia, are not post-mitotic precursors per se, are not stem cells per se, and/or are not a single isolated cell type per se.

Mammalian fetal retinal cells or RPC cells are not found in the early embryo (e.g., the blastocyst). Additionally, mammalian fetal retinal cells or RPC cells are not found in any useful abundance in the normal mature mammal (e.g., human).

In addition, retinal progenitor cells do not persist for the life of the organism. However, these mammalian fetal retinal cells or RPC cells are found in their native abundance in the developing (fetal) mammalian (e.g., human) retina.

While mammalian fetal retinal cells or RPC are mostly mitotic when grown under proliferation conditions, a minority admixture of post-mitotic cells may also be included in any of the compositions and populations described herein.

The mammalian fetal retinal cells or RPC cells are immunologically tolerated as ocular allografts in unrelated mammals, e.g., humans. Thus, the RPCs have low immunogenicity when placed in the eye. By way of non-limiting example, these mammalian fetal retinal cells or RPC cells can be grafted to a vitreous cavity or in a subretinal space for mammalian, or human, vision or retinal disease therapeutic and/or prophylactic therapy.

In alternative embodiments, the mammalian fetal retinal cells or RPC cells do not come with any risk (or without a substantial risk) of tumor formation or other unwanted cell growth.

The mammalian fetal retinal cells or RPC cells can be cultured as spheres or adherent monolayers, or as spheres and then monolayers, and/or as a combination of spheres and monolayers. However, spheres are not required, and, in some embodiments, the cells are grafted as dissociated cells, not as spheres, or as a mixture of both dissociated cells and spheres. The mammalian fetal retinal cells or RPC cells contain grafted cells that coalesce in the vitreous and, optionally, can become spheres.

In alternative embodiments, retinal progenitor cells and cell populations containing them are not immortal, nor are they allowed to immortalize, or forced to immortalize. While the cells do not proliferate indefinitely, the exemplary cell culture methods described herein can improve the proliferation rate and duration and/or can improve donor cell yield significantly for a given tissue donation. As used herein, an "immortal" cell line is a cell line that can divide indefinitely, while a "non-immortal" cell line is able to divide for a limited number of passages. For example, non-immortal retinal progenitor cells may be able to divide through 1, 2, 3, 4, 5, 6, 7, 8, 9, 10, 11, 12, 13, 14, 15, 16, 17, 18, 19, 20, 25, 30 or more passages.

RPCs can either be non-genetically modified cells, or they can be genetically modified (e.g., transformed stably or transiently, or inducibly) using any method(s) known in the art. For example, retinal progenitor cells can be genetically modified to express one or more heterologous or exogenous nucleic acid sequences of interest. A nucleic acid sequence can be "exogenous," which means that it is foreign to the cell into which the vector is being introduced or that the sequence is homologous to a sequence in the cell but in a position within the host cell nucleic acid in which the sequence is ordinarily not found. Nucleic acid sequences include plasmids, amplicons, cDNA, mRNA, antisense RNA, siRNA, but are not limited to these examples. The term "gene" refers to a functional protein, polypeptide, or peptide-encoding nucleic acid unit. As will be understood by those in the art, this functional term includes genomic sequences, cDNA sequences, and smaller engineered gene segments that express, or may be adapted to express, proteins, polypeptides, domains, peptides, fusion proteins, and mutants.

Any methodology known in the art can be used for genetically altering the cells. One exemplary method is to insert a gene into the cells of the tissue with a recombinant viral vector. Any one of a number of different vectors can be used, such as viral vectors, plasmid vectors, linear DNA, etc., as known in the art, to introduce an exogenous nucleic acid fragment encoding for a therapeutic agent into target cells and/or tissue. These vectors can be inserted, for example, using any of infection, transduction, transfection, calcium-phosphate mediated transfection, DEAE-dextran mediated transfection, electroporation, liposome-mediated transfection, biolistic gene delivery, liposomal gene delivery using fusogenic and anionic liposomes (which are an alternative to the use of cationic liposomes), direct injection, receptor-mediated uptake, magnetoporation, ultrasound and others as known in the art.

As used herein, a "vector" refers to a carrier nucleic acid molecule into which a nucleic acid sequence can be inserted for introduction into a cell where it can be replicated. Vectors include plasmids, cosmids, viruses (bacteriophage, animal viruses, and plant viruses), and artificial chromosomes (e.g., YACs). One of skill in the art would be well equipped to construct a vector through standard recombinant techniques, which are described in Sambrook et al. (1989) Molecular Cloning: A Laboratory Manual, Cold Spring Harbor, N.Y.; Ausubel et al. (1987) Current Protocols in Molecular Biology, Greene Publ. Assoc. & Wiley-Intersciences. In addition to encoding a modified polypeptide, a vector may encode non-modified polypeptide sequences such as a tag or targeting molecule. Useful vectors encoding such fusion proteins include pIN vectors, vectors encoding a stretch of histidines, and pGEX vectors, for use in generating glutathione S-transferase (GST) soluble fusion proteins for later purification and separation or cleavage.

Vectors may be designed primarily to introduce into cells a heterologous nucleic acid molecule, such as a gene that is "operably linked" or under the control of one or more control sequences. A "promoter" refers to one or more transcriptional control modules that are clustered around the initiation site for RNA polymerase II and other transcriptional activator proteins. Any promoter/enhancer combination (as per the Eukaryotic Promoter Data Base EPDB) could also be used to drive expression of a nucleic acid molecule of interest (i.e., constitutive, inducible, repressible, tissue specific). Also, the vectors may contain a selectable marker to facilitate their manipulation in vitro or ex vivo. Vectors may also contain a polyadenylation signal, which may be obtained from the human growth hormone (hGH) gene, the bovine growth hormone (BGH) gene, or SV40. In addition, vectors may also contain internal ribosome binding sites (IRES) elements are used to create multigene, or polycistronic, messages. IRES elements are able to bypass the ribosome scanning model of 5-methylated cap-dependent translation and begin translation at internal sites (Pelletier, J. and Sonenberg, N. (1988) Nature 334(6180): 320-325). IRES elements can be linked to heterologous open reading frames. Multiple open reading frames can be transcribed together, each separated by an IRES, creating polycistronic messages. By virtue of the IRES element, each open reading frame is accessible to ribosomes for efficient translation. Multiple genes can be efficiently expressed using a single promoter/enhancer to transcribe a single message.

In some embodiments, the vector is a viral vector. Viral vectors known in the art include, without limitation, adenoviral vectors, retroviral vectors, vaccinia viral vectors, adeno-associated viral (AAV) vectors, polyoma viral vectors, alphaviral vectors, rhabdoviral vectors, lentiviral vectors, Epstein-Barr viral vectors, picornaviral vectors, or herpesviral vectors. In those embodiments where the viral vector is an AAV vector, any serotype of AAV vector known in the art may be used. For example, the AAV vector may be AAV1, AAV2, AAV4, AAV5, AAV8 or AAV9. The AAV may be pseudotyped, mixing a capsid protein and viral genome from different viral serotypes (e.g. inverted terminal repeats from one AAV serotype, and a capsid from a different serotype).

In other embodiments, a nucleic acid sequence may be entrapped in a liposome or lipid formulation. Liposomes are vesicular structures characterized by a phospholipid bilayer membrane and an inner aqueous medium. Multilamellar liposomes have multiple lipid layers separated by aqueous medium. They form spontaneously when phospholipids are suspended in an excess of aqueous solution. The lipid components undergo self-rearrangement before the formation of closed structures and entrap water and dissolved solutes between the lipid bilayers (Ghosh, P. C. and Bachhawat, B. K. (1991) Targeted Diagn. Ther. 4: 87-103). One example of a commercially available liposomes or lipid formulations is Lipofectamine (Invitrogen). Others include FuGENE (Promega), PromoFectin (PromoKine), Affectene (Qiagen), Polyfect (Qiagen), Superfect (Qiagen), and TransMessenger (Qiagen).

Isolation of Primary Retinal Cells

Provided herein are methods for isolating, culturing and/or using dissociated suspensions of fetal retinal cells, e.g., human primary retinal cells from a sample. In various embodiments, the suspensions of fetal retinal cells do not include tissue or scaffolds. Also provided are methods for the isolation and characterization of retinal progenitor cells and compositions containing such cells that are harvested from a donor tissue, grown in culture, and formulated for administration to a subject or patient.

The methods described herein for isolating primary retinal cells from a human sample does not require the use of a protease to digest the plurality of primary retinal cells, which results in greater number of viable primary retinal cells as compared to a method that uses a protease, or a combination of mechanical dissociation and protease digestion.

In one aspect, the disclosure provides method of isolating primary retinal cells from a human sample comprising: (a) isolating a retinal sample comprising a plurality of primary retinal cells from the human sample, (b) mechanically dissociating the plurality of primary retinal cells in the retinal sample isolated in step (a), thereby generating a dissociated suspension of cells and cell clusters, and (c) determining the viability, quantity, morphology or a combination thereof of the primary retinal cells from the retinal sample. Human samples are isolated from human donors. The donor can be 17 to about 20 weeks of age. In some embodiments, the methods of isolating primary retinal cells described herein produce at least $30 \times 10^6$ viable primary retinal cells, which are then cultured to produce retinal progenitor cells.

In some embodiments, the sample is an eye or a pair of eyes isolated from a mammal, for example a mouse, a rat, a rabbit, a cat, a dog, a monkey, a non-human primate, or a human. In some embodiments, the sample is from an agricultural animal, for example a horse, a cow, or a sheep.

Samples used for isolating and/or culturing cell populations may be harvested from healthy subjects (i.e., individuals not harboring a retinal disease), from diseased subjects, and may include not only fresh retinal cell populations, but also frozen retinal cell populations. Sources include, without limitation, whole eyes, or retinal tissues, or other sources, obtained from embryonic, fetal, pediatric or adult tissue. The methods described herein can include further enrichment or purification procedures or steps for cell isolation by positive selection for other retinal progenitor cell specific markers. The retinal progenitor cells and cell populations may be obtained or harvested from any mammalian species or subjects, e.g. human, primate, equine, bovine, porcine, canine, feline, ferret, rabbit, rodent, e.g. mice, rats, hamster, etc.

In some embodiments, cells are harvested from a mammalian fetal retina at a stage after which the retina is formed, but before photoreceptor outer segments are fully formed throughout the retina and before retinal vascularization has been completed or substantially completed. The stages are typically between fetal gestational ages of about 12 weeks to about 28 weeks (e.g., about 12, 13, 14, 15, 16, 17, 18, 19, 20, 21, 22, 23, 24, 25, 26, 27, or 28 weeks) in a human fetus. In some embodiments, the stage can be 17 weeks to about 20 weeks gestational age. For non-human cells from larger mammals, such as feline or porcine retinal progenitor cells, the stages are typically between fetal gestational ages of about 3 weeks to about 11 weeks (e.g., about 3, 4, 5, 6, 7, 8, 9, 10, or 11 weeks). See, for example, Anand-Apte, B. and Hollyfield, J. G. "Developmental Anatomy of the Retinal and Choroidal Vasculature." In The Retina and Its Disorders, Besharse, J. and Bok, D., Academic Press, (2001). However, cells can also be harvested from postnatal or neonatal mammalian tissue.

In some embodiments, the sample is a human sample. In some embodiments, the human sample is one or a pair of eyeballs from a human donor. In some embodiments, the human donor is of about 12 weeks to about 28 weeks gestational age. In some embodiments, the human donor is of about 17 weeks to about 20 weeks gestational age. In some embodiments, use of a narrower donor age range improves consistency of the final yield of retinal progenitor cells during manufacturing.

In some embodiments, the sample is one or a pair of human fetal eyeballs. In some embodiments, the eyeballs possess a normal morphology. Normal morphology can be determined by visual inspection for features such as intact globe(s), clear cornea, a normal shape, or any combination of these features.

In some embodiments, the human retinal tissue can be shipped on ice and delivered within a transportation window. The transportation window can include holding the cells at a destination or point of departure for a period of time, for example on ice or in a fridge at a temperature of between about 1-8° C., or at about 4° C. In some embodiments, the transportation window is between about 1 and 40 hours, between about 7 and 40 hours, between about 1 and 34 hours, between about 7 and 34 hours, between about 1 and 26 hours, between about 4 and 26 hours, between about 7 and 26 hours, between about 8 and 26 hours, between about 4 and 18 hours, between about 7 and 18 hours, or between about 8 and 18 hours. In some embodiments, the transportation window is about 1 hour, about 2 hours, about 2.5 hours, about 3 hours, about 3.5 hours, about 4 hours, about 4.5 hours, about 5 hours, about 5.5 hours, about 6 hours, about 6.5 hours, about 7 hours, about 7.5 hours, about 8 hours, about 8.5 hours, about 9 hours, about 10 hours, about 11 hours, about 12 hours, about 13, hours, about 14 hours, about 15 hours, about 16 hours, about 17 hours, about 18 hours, about 19 hours, about 20 hours, about 21 hours, about 22 hours, about 23 hours, about 24 hours, about 25 hours or about 26 hours. By way of non-limiting example, the transportation window may be from about 1 to about 26 (e.g., 1, 1.5, 2, 2.5, 3, 3.5, 4, 4.5, 5, 5.5, 6, 6.5, 7, 7.5, 8, 8.5, 9, 9.5, 10, 10.5, 11, 11.5, 12, 12.5, 13, 13.5, 14, 14.5, 15, 15.5, 16, 16.5, 17, 17.5, 18, 18.5, 19, 19.5, 20, 20.5, 21, 21.5, 22, 22.5, 23, 23.5, 24, 24.5, 25, 25.5, or 26), for example from about 4.5 to about 21.5 hours (e.g., 1, 1.5, 2, 2.5, 3, 3.5, 4, 4.5, 5, 5.5, 6, 6.5, 7, 7.5, 8, 8.5, 9, 9.5, 10, 10.5, 11, 11.5, 12, 12.5, 13, 13.5, 14, 14.5, 15, 15.5, 16, 16.5, 17, 17.5, 18, 18.5, 19, 19.5, 20, 20.5, 21, or 21.5) or from about 7 to about 26 hours (e.g., 7, 7.5, 8, 8.5, 9, 9.5, 10, 10.5, 11, 11.5, 12, 12.5, 13, 13.5, 14, 14.5, 15, 15.5, 16, 16.5, 17, 17.5, 18, 18.5, 19, 19.5, 20, 20.5, 21, 21.5, 22, 22.5, 23, 23.5, 24, 24.5, 25, 25.5, or 26 hours).

In some embodiments, the sample is placed into a mammalian cell culture medium after harvest from the donor. Mammalian cell culture media that can be used during transportation of the sample include both basal cell culture media and complex cell culture media. Non-limiting examples of basal cell culture media used during transportation include, but are not limited to, Minimum Essential Medium Eagle, ADC-1, LPM (Bovine Serum Albumin-free), F10 (Ham), F12 (Ham), DCCM1, DCCM2, RPMI 1640, BGJ Medium (with and without Fitton-Jackson Modification), Basal Medium Eagle (BME—with the addition of Earle's salt base), Dulbecco's Modified Eagle Medium (DMEM—without serum), Advanced DMEM/F-12, Yamane, IMEM-20, Glasgow Modification Eagle Medium (GMEM), Leibovitz L-15 Medium, McCoy's 5A Medium, Medium M199 (M199E—with Earle's sale base), Medium M199 (M199H—with Hank's salt base), Minimum Essential Medium Eagle (MEM-E—with Earle's salt base), Minimum Essential Medium Eagle (MEM-H—with Hank's salt base) and Minimum Essential Medium Eagle (MEM-NAA with non-essential amino acids), among numerous others, including medium 199, CMRL 1415, CMRL 1969, CMRL 1066, NCTC 135, MB 75261, MAB 8713, DM 145, Williams'G, Neuman & Tytell, Higuchi, MCDB 301, MCDB 202, MCDB 501, MCDB 401, MCDB 411, MDBC 153, and Ultraculture. In some embodiments, the cell culture medium used for transportation comprises RPMI-1640. In some embodiments, the cell culture medium used for transportation comprises RPMI 1640 supplemented with L-Glutamine. In some embodiments, the cell culture medium used for transportation comprises Advanced DMEM/F-12. In some embodiments, the cell culture medium used for transportation comprises a complete medium. For example, the cell culture medium used for transportation comprises a basal medium supplemented with one or more of N-2 supplement, B27 xeno-free, B27, StemPro, epidermal growth factor (EGF), basic fibroblast growth factor (bFGF), or GlutaMAX I. In some embodiments, the cell culture medium used for transportation comprises one or more antibiotics. For example, the cell culture medium used for transportation comprises Gentamicin at between about 30 to 100 micrograms (μg) per milliliter (mL), or between about 0.5 to about 50 μg/mL. In some embodiments, the cell culture medium used for transportation comprises Gentamicin at about 50 μg/mL.

In some embodiments, the human sample is stored at about 1 to 8° C. immediately after placement in the transport cell culture medium. In some embodiments, the human sample is stored at about 4° C. immediately after placement in the transport cell culture medium. For example, the human sample is stored on ice immediately after placement in the transport cell culture medium.

The disclosure provides methods of isolating a retinal sample comprising a plurality of primary retinal cells from the human sample, for example a sample comprising one or a pair of eyeballs from a human donor of about 12-28 weeks gestational age.

Retinal progenitor cells can be purified from other tissue components after or concurrent with the processing of a tissue sample. For example, progenitor cells can be purified from other cells and tissue components after the tissue sample has been cultured under conditions suitable for cell growth and for a time sufficient to allow cells to adhere to the culture dish. In certain embodiments, purification of cells involves obtaining cells that migrate from the tissue sample during culture and are present in the culture media or loosely adhered to a fibronectin or other substrate, or a feeder cell layer. These cells may be obtained by routine methods, such as removing and centrifuging the media to pellet cells therein, and washing the cells remaining in the culture dish with a solution such as phosphate-buffered saline (PBS) or Hanks Balanced Salt Solution to remove those cells loosely attached as an adherent cell layer. This wash solution may then also be centrifuged to obtain cells. Purification of retinal progenitor cells and cell populations may further involve separating cells from certain insoluble tissue components, including residual tissue material, such as lipids. Cells may be separated from other tissue components by any means known and available in the art, including, e.g., the use of density gradients, centrifugation, sorting by flow cytometry or magnetic cell separation (MACS), and filtration or combinations thereof. Examples of specific methods of purifying cells are known and described in the art, e.g., in U.S. Pat. No. 6,777,231. Negative separation methods can also be employed to remove one or more particular types of cells.

Tissue may also be processed or "dissociated". For example, tissue such as one or a pair of eyeballs may be processed or dissected to isolate the retinas, and the retinas dissociated to produce a plurality of primary retinal cells and cell clusters. These primary retinal cells and cell clusters are then cultured as described herein to produce a plurality of retinal progenitor cells.

Accordingly, the disclosure provides methods of isolating a retinal sample comprising a plurality of primary retinal cells from a human sample. The human sample comprises, for example, one or a pair of eyeballs from a human donor between about 12 and 28 weeks gestational age. In some embodiments, the methods comprise: (i) removing the one or pair of human eyeballs from the transport culture medium, (ii) rinsing the one or pair of human eyeballs with about 1-8° C. phosphate buffered saline (PBS) supplemented with antibiotic, (iii) removing an optic nerve and mesenchymal tissue from the one or a pair of human eyeballs, (iv) washing the one or pair of human eyeballs with about 1-8° C. PBS supplemented with an antibiotic, (v) puncturing a globe of each of the one or pair of human eyeballs at the limbus using a needle, (vi) circumferentially cutting along a limbus of the one or pair of human eyeballs, for example using a pair of microscissors, (vii) removing a lens, cornea, and associated vitreous body from the one or pair of human eyeballs, (viii) dissociating the retina(s) from the retinal pigment epithelium (RPE) layer to produce an isolated retina or pair of isolated retinas, and (ix) placing the isolated retina or pair of isolated retinas in about 1-8° C. culture medium or PBS, wherein the culture medium or PBS is supplemented with an antibiotic. Rinsing (or washing) the sample at various steps can be repeated between 1-5 times, or more. For example, the sample can be rinsed 1, 2, 3, 4, or 5 times. In some embodiments, the retinal sample produced by the methods described herein is free, or substantially free, of extra-ocular cells.

In some embodiments, the retinal samples isolated using the methods described herein are dissociated to produce isolated retinal cells and clusters of retinal cells, which are cultured to produce retinal progenitor cells. In some embodiments, the dissociation of the retinal sample is mechanical. In some embodiments, the dissociation comprises (i) transferring the retinal sample to a tube, (ii) mechanically dissociating the retinal sample to produce a plurality of dissociated primary retinal cells, (iii) pelleting the plurality of dissociated primary retinal cells via centrifugation, and (iv) removing the supernatant. Mechanical dissociation can be accomplished by any means known in the art, including but not limited to, trituration with a sterile pipet. In some embodiments, the trituration is performed multiple times, e.g. between 2 and 50 times, between 2 and 10 times, or between 2 and 8 times, or until the retinal sample is broken into cell clusters of suitable size. In some embodiments, the trituration is performed between 4 and 8 times.

In some embodiments, dissociation of the retinal sample comprises digestion with a protease. In some embodiments, dissociation of the retinal sample comprises digestion with a protease and mechanical dissociation. In some embodiments, the protease is trypsin. Suitable trypsin compositions will be known to persons of ordinary skill in the art and include, but are not limited to, TrypLE (Thermo Fisher Scientific), TrypLE Select (Invitrogen) and TrypLE Express (Invitrogen). For example, isolated retinas can be pipetted in undiluted TrypLE Express. The activity or proteases such as trypsin can be neutralized by the addition an excess of protease-free medium to halt the reaction. For example, a 5×, 10×, 15×, or 20× excess of culture medium can be added to the mixture comprising the dissociated retinas.

Dissociation may be carried out by physical dissociation and/or by exposure to an enzyme preparation that facilitates the release of cells from other tissue components to create a "dissociated suspension" of cells and/or cell clusters. Examples of such enzymes include, but are not limited to, matrix metalloproteinases, clostripain, papain, trypsin, trypsin-like, pepsin, pepsin-like, neutral protease-type and collagenases. Suitable proteolytic enzymes are described in U.S. Pat. Nos. 5,079,160; 6,589,728; 5,422,261; 5,424,208; and 5,322,790. For example, the enzyme preparation may include trypsin alone or in combination with one or more additional enzymes. Enzymatic dissociation may be carried out in conjunction with physical dissociation by, for example, mincing, pipetting, chopping, homogenizing, grinding, freeze-thawing, osmotically shocking, to remove unwanted cells or connective tissue and ultimately resulting in single cell cultures or may include cell clusters that can be defined by size, i.e., "small", "medium" and "large". Cell cluster size is subjective and may vary in the practice of the subject matter disclosed herein. The isolated primary retinal cells described herein comprise isolated cells and clusters of cells. Clusters of isolated primary retinal cells can be between about 2-5000 cells, between 2-4000 cells, between 2-3000 cells, between 2-2000 cells, between 2-1000 cells, between 2-100 cells, between 50-5000 cells, between 50-4000 cells, between 50-3000 cells, between 50-2000 cells, between 50-1000 cells, between 50-100 cells, between 500-5000 cells, or between 500-1000 cells.

Compositions comprising pluralities of isolated primary retinal cells can be pelleted via centrifugation in order to concentrate the cells, to wash or rinse the cells, or to change the cell culture medium. For example, pluralities of dissociated primary retinal cells may be washed culture medium or PBS, optionally supplemented with antibiotic. Pluralities of dissociated primary retinal cells may be pelleted via centrifugation between about 100×g (centrifugal force) and about 1000×g, between about 100×g and about 500×g between about 140×g and about 300×g. In some embodiments, the plurality of dissociated primary retinal cells is pelleted via centrifugation at about 140×g. In some embodiments, the plurality of dissociated primary retinal cells is pelleted via centrifugation at about 300×g. Centrifugation can be for between about 1 minute and 30 minutes. For example, compositions comprising pluralities of isolated primary retinal cells can be centrifuged for about 1, 2, 3, 4, 5, 6, 7, 8, 9, 10, 15, 20, 25 or 30 minutes. Centrifugation can be at any temperature necessary to maintain cell viability. In some embodiments, compositions comprising pluralities of isolated primary retinal cells are centrifuged at between about 0° C. and 50° C. In some embodiments, compositions comprising pluralities of isolated primary retinal cells are centrifuged at about 4° C. In some embodiments, compositions comprising pluralities of isolated primary retinal cells are centrifuged at about 18-24° C. In some embodiments, compositions comprising pluralities of isolated primary retinal cells are centrifuged at about 37° C.

In some embodiments of the methods described herein, the methods comprise (i) resuspending the dissociated, pelleted primary retinal cells in about 1-8° C. antibiotic-supplemented culture medium, (ii) seeding the plurality of dissociated retinal cells into one or more coated cell culture flasks or plates containing culture medium, optionally wherein the cell culture medium is supplemented with an antibiotic, (iii) incubating the plurality of dissociated retinal cells at about 10 to 50° C., optionally wherein the incubation occurs at about 37° C., and (iv) determining the quantity and viability of primary retinal cells and retinal cell clusters. Flasks or plates can be seeded at any appropriate density. For example, flasks or plates can be seeded with between about 1 and about 1,000,000,000 cells. Alternatively, flasks or plates can be seeded at about 10,000 to about $5 \times 10^6$ cells per square centimeter ($cm^2$). As a further alternative, flasks or plates can be seeded at about $0.50 \times 10^6$ to about $2.5 \times 10^6$ cells per square centimeter ($cm^2$). As a further alternative, flasks or plates can be seeded at about $0.82 \times 10^6$ to about $2.06 \times 10^6$ cells per square centimeter ($cm^2$). As a further alternatives, flasks or plates can be seeded at about $0.1 \times 10^6$ to about $20 \times 10^6$ cells per $cm^2$, about $1 \times 10^6$ to about $20 \times 10^6$ cells per $cm^2$, about $2 \times 10^6$ to about $20 \times 10^6$ cells per $cm^2$, about $3 \times 10^6$ to about $20 \times 10^6$ cells per $cm^2$, about $4 \times 10^6$ to about $20 \times 10^6$ cells per $cm^2$, about $5 \times 10^6$ to about $20 \times 10^6$ cells per $cm^2$, about $6\times10^6$ to about $20\times10^6$ cells per cm$^2$, about $7\times10^6$ to about $20\times10^6$ cells per cm$^2$, about $8\times10^6$ to about $20\times10^6$ cells per cm$^2$, about $9\times10^6$ to about $20\times10^6$ cells per cm$^2$, about $10\times10^6$ to about $20\times10^6$ cells per cm$^2$, about $0.2\times10^6$ to about $10\times10^6$ cells per cm$^2$, about $0.2\times10^6$ to about $5\times10^6$ cells per cm$^2$, about $0.2\times10^6$ to about $4\times10^6$ cells per cm$^2$, about $0.2\times10^6$ to about $3\times10^6$ cells per cm$^2$, about $0.2\times10^6$ to about $2\times10^6$ cells per cm$^2$, about $0.5\times10^6$ to about $10\times10^6$ cells per cm$^2$, about $0.5\times10^6$ to about $5\times10^6$ cells per cm$^2$, about $0.5\times10^6$ to about $4\times10^6$ cells per cm$^2$, about $0.5\times10^6$ to about $3\times10^6$ cells per cm$^2$, or about $0.5\times10^6$ to about $2.5\times10^6$ cells per cm$^2$.

In some embodiments, the methods described herein produce between about $20\times10^6$ and about $1\times10^9$ viable primary retinal cells, between about $20\times10^6$ and about $1\times10^8$ viable primary retinal cells, between about $20\times10^6$ and about $1\times10^7$ viable primary retinal cells, about $30\times10^6$ and about $1\times10^9$ viable primary retinal cells, between about $30\times10^6$ and about $1\times10^8$ viable primary retinal cells, between about $30\times10^6$ and about $1\times10^7$ viable primary retinal cells, between about $20\times10^6$ and about $147\times10^6$ viable primary retinal cells, between about $20\times10^6$ and about $100\times10^6$ viable primary retinal cells, or between about $73\times10^6$ and about $147\times10^6$ viable primary retinal cells. In some embodiments, the methods described herein produce at least about $20\times10^6$ viable primary retinal cells. In some embodiments, the methods described herein produce at least about $30\times10^6$ viable primary retinal cells. In some embodiments, the methods described herein produce at least about $35\times10^6$ viable primary retinal cells. In some embodiments, the methods described herein produce at least about $30\times10^6$ viable primary retinal cells. In some embodiments, the methods described herein produce at least about $45\times10^6$ viable primary retinal cells. In some embodiments, the methods described herein produce at least about $50\times10^6$ viable primary retinal cells. In some embodiments, the methods described herein produce at least about $20\times10^6$ viable primary retinal cells, at least about $30\times10^6$ viable primary retinal cells, at least about $40\times10^6$ viable primary retinal cells, at least about $50\times10^6$ viable primary retinal cells, at least about $60\times10^6$ viable primary retinal cells, at least about $70\times10^6$ viable primary retinal cells, at least about $80\times10^6$ viable primary retinal cells, at least about $90\times10^6$ viable primary retinal cells, at least about $100\times10^6$ viable primary retinal cells, at least about $120\times10^6$ viable primary retinal cells, at least about $140\times10^6$ viable primary retinal cells, at least about $145\times10^6$ viable primary retinal cells, at least about $147\times10^6$ viable primary retinal cells, at least about $150\times10^6$ viable primary retinal cells, at least about $170\times10^6$ viable primary retinal cells, at least about $190\times10^6$ viable primary retinal cells or at least about $200\times10^6$ viable primary retinal cells.

Cell Morphology, Number and Viability

Provided herein are methods for determining the viability, quantity, and morphology of the primary retinal cells from the retinal sample, and of retinal progenitor cells produced from primary retinal cells.

Morphology of cells can be determined via light microscopy using any suitable method. Suitable light microscopy methods will be known to persons of ordinary skill in the art, and include, but are not limited to, differential interference contrast, Nomarski, Hoffman modulation contrast and variations thereof, fluorescence microscopy and confocal microscopy. Optionally, histochemical staining for one or more markers of isolated primary retinal cells may be used.

Cell number and viability can be measured using an NC200 Automated Cell Counter (Chemometec) and the aggregate cell counting method. Alternatively, or in addition, cell number and viability can be measured using Trypan Blue, or a hemocytometer.

In some embodiments, the percentage of viable counted cells is between about 10% and about 100%, or between about 68% and about 85%.

Mammalian fetal retinal or RPC cells express quantitatively different gene profiles, e.g., as described herein; or they express quantitatively different soluble factor profiles; or they express quantitatively different surface marker profiles. Moreover, mammalian fetal retinal cells or RPC cells have a gene profile that is not fixed, constant or immutable. Rather, they have a gene profile that dynamically changes quantitatively with time in culture.

The subject matter disclosed herein relates to a cell population containing mammalian retinal progenitor cells that are isolated according to a defined cell culture method and which express characteristic markers. The cell population may be a culture of cells isolated from a mammal and grown in vitro. For example, the culture may include a suspension of cells or adherent cells cultured in a culture plate, dish, flask, or bioreactor. The sample may be homogeneous or heterogeneous, which may be determined by expression of one or more markers as defined herein. The cell population disclosed herein is a mixed cell population and may contain a mixture of undifferentiated and differentiated cells. Relative expression levels of markers characteristic of the retinal progenitor cells defined herein may vary between cells within the population.

Retinal progenitor cells may be characterized by their expression of molecular markers, including cell surface markers and non-surface ("genetic") markers. While it is common in the art to refer to cells as "positive" or "negative" for a particular marker, actual expression levels are a quantitatively determined. The number of molecules on the cell surface (or located elsewhere) can vary by several logs, yet still be characterized as "positive". It is also understood by those of skill in the art that a cell which is negative for staining, i.e. the level of binding of a marker specific reagent is not detectably different from a control, e.g. an isotype matched control, may express minor amounts of the marker. Characterization of the level of labeling ("staining") permits subtle distinctions between cell populations. The staining intensity of cells can be monitored by flow cytometry, where lasers detect the quantitative levels of fluorochrome (which is proportional to the amount of cell surface marker bound by specific reagents, e.g. antibodies). Flow cytometry, or FACS, can also be used to separate cell populations based on the intensity of binding to a specific reagent, as well as other parameters such as cell size and light scatter. Although the absolute level of staining may differ with a particular fluorochrome and reagent preparation, the data can be normalized to a control.

To normalize the distribution to a control, each cell is recorded as a data point having a particular intensity of staining. These data points may be displayed according to a log scale, where the unit of measure is arbitrary staining intensity. By way of example, the brightest stained cells in a sample can be as much as 4 logs more intense than unstained cells. When displayed in this manner, cells falling in the highest log of staining intensity are bright, while those in the lowest intensity are negative. The "low" positively stained cells have a level of staining above the brightness of an isotype matched control, but are not as intense as the most brightly staining cells normally found in the population. Low positive cells may have unique properties that differ from the negative and brightly stained positive cells of the sample. An alternative control may utilize a substrate having a defined density of marker on its surface, for example a fabricated bead or cell line, which provides the positive control for intensity.

Expression of markers may be subject to change during culture of retinal tissue from which the retinal progenitor cells and cell populations are derived. For example, differences in marker expression can be influenced by culture conditions such as oxygen levels (e.g., atmospheric oxygen conditions, or "normoxic" conditions; or low oxygen conditions, also known as "hypoxic" conditions). By way of non-limiting example, the low oxygen conditions may include about 0.5%-10% oxygen (e.g., about 0.5, 1, 1.5, 2, 2.5, 3, 3.5, 4, 4.5, 5, 5.5, 6, 6.5, 7, 7.5, 8, 8.5, 9, 9.5, or 10%). In some embodiments, the low oxygen conditions may include about 0.5%-5%, about 1%-5%, or about 1%-3%. Those of ordinary skill in the art will be aware that marker expression of the retinal progenitor cells and cell populations is not static and may change as a function of one or more culture conditions, e.g., culture media, oxygen levels, number of passages, time in culture, etc.

Retinal progenitor cells and cell populations may express one or more, two or more, three or more, four or more, five or more, six or more, seven or more, eight or more, nine or more, ten or more, eleven or more, twelve or more, thirteen or more, fifteen or more, sixteen or more, seventeen or more, eighteen or more, nineteen or more, twenty or more, twenty-five or more, thirty or more of the markers defined herein, or any increment in between up to fifty or more markers.

Culturing Primary Retinal Cells and Retinal Progenitor Cells (RPCs)

Provided herein are methods of culturing primary retinal cells and retinal progenitor cells to produce populations of retinal progenitor cells for transplant and therapeutic applications.

The methods described herein can produce large quantities of viable cells. For example, the methods described herein can produce about 1 billion retinal progenitor cells or more at harvest. In some embodiments, at least 50%, at least 60%, at least 70%, at least 80% or at least 90% of the cells are viable.

In some embodiments, donor cells can be cultured without antibiotics in order to avoid altering cells. Moreover, without antibiotics, use of very low passage cells is possible since occult microbial contamination can be ruled out. In alternative embodiments, use of low passage cells has a low risk of transformation and/or tumor formation. Additionally, use of low passage cells are closest to the natural cells present in the developing retina.

In some embodiments, primary retinal cells and retinal progenitor cells are cultured with the use of an antibiotic. Suitable antibiotics include, but are not limited to, Penicillin, Streptomycin and Gentamicin. In some embodiments, the antibiotic comprises Gentamicin. In some embodiments, the Gentamicin is at a concentration between about 0.5 and 50 µg/mL, e.g., about 0.5 and 40 µg/mL, about 5 and 50 µg/mL, or about 5 and 35 µg/mL. In some embodiments, the Gentamicin is at a concentration of about 50 µg/mL. In some embodiments, the Gentamicin is at a concentration of about 30 µg/mL.

Any suitable basal media can be used for growth and culture of RPCs. Cell culture describes a process by which cells are grown under controlled conditions, generally outside of their natural environment. Cell populations are grown or cultured in any cell culture medium known in the art. The term "basal medium" refers to any medium that can support cell growth. The basal medium provides standard inorganic salts such as zinc, iron, magnesium, calcium, and potassium, vitamins, glucose, buffer system, and key amino acids. The basal medium that can be used in the present invention includes, but is not limited to, Minimum Essential Medium Eagle, ADC-1, LPM (Bovine Serum Albumin-free), F10 (Ham), F12 (Ham), DCCM1, DCCM2, RPMI 1640, BGJ Medium (with and without Fitton-Jackson Modification), Basal Medium Eagle (BME—with the addition of Earle's salt base), Dulbecco's Modified Eagle Medium (DMEM—without serum), Yamane, IMEM-20, Glasgow Modification Eagle Medium (GMEM), Leibovitz L-15 Medium, McCoy's 5A Medium, Medium M199 (M199E—with Earle's sale base), Medium M199 (M199H—with Hank's salt base), Minimum Essential Medium Eagle (MEM-E—with Earle's salt base), Minimum Essential Medium Eagle (MEM-H—with Hank's salt base) and Minimum Essential Medium Eagle (MEM-NAA with non-essential amino acids), among numerous others, including medium 199, CMRL 1415, CMRL 1969, CMRL 1066, NCTC 135, MB 75261, MAB 8713, DM 145, Williams'G, Neuman & Tytell, Higuchi, MCDB 301, MCDB 202, MCDB 501, MCDB 401, MCDB 411, MDBC 153, and Ultraculture. In alternative embodiments, media for use in culturing the retinal progenitor cells disclosed herein are Advanced DMEM/F12 and Ultraculture. A number of these media are summarized in Methods in Enzymology, Volume LVIII, "Cell Culture," pp. 62-72.

In some embodiments, the medium comprises Dulbecco's Modified Eagle Medium DMEM/F12, Advanced DMEM/F12, Knockout DMEM/F12, Neurobasal media, ReNcell or Ultraculture media. In some embodiments, the medium comprises DMEM/F12.

"Conditioned medium" refers to a medium that is altered as compared to a base or basal medium. For example, the conditioning of a medium may cause molecules, such as nutrients and/or growth factors, to be added to or depleted from the original levels found in the base medium. A medium can be conditioned by allowing cells of certain types to be grown or maintained in the medium under certain conditions for a certain period of time. For example, a medium can be conditioned by allowing retinal progenitor cells to be expanded, differentiated or maintained in a medium of defined composition at a defined temperature for a defined number of hours. As will be appreciated by those of skill in the art, numerous combinations of cells, media types, durations and environmental conditions can be used to produce nearly an infinite array of conditioned media.

Examples of cell culture supplements or additives include, without limitation, ingredients to replace partly or wholly the role of serum in supporting cell survival or growth. For example, supplements may include insulin, transmetalloproteins, trace elements, vitamins, or other factors. These factors are generally not included in the basal medium but are provided by serum used generally in culturing cells. The supplement or additive may include at least one or more of the following components that support cell growth: one or more insulins or replacements thereof, one or more transmetalloproteins or replacements thereof, one or more trace elements (e.g., selenium, iron, zinc, copper, cobalt, chromium, iodine, fluoride, manganese, molybdenum, vanadium, nickel, tin), one or more vitamins (e.g., Vitamin C, Vitamin E, Vitamin A, Vitamin B-group), one or more salts (e.g., sodium salts, magnesium salts, calcium salts, or phosphate salts), one or more buffers (e.g., phosphate buffered saline, HEPES buffer), one or more amino acids (e.g., L-glutamine), one or more hormones, hormone-like compounds or growth factors (such as, e.g., transferrin, EGF, NGF, ECGF, PDGF, FGF, IGF, LIF, interleukins, interferons, TGF, and/or VEGF, glucagon, corticosteroids, vasopressin, prostaglandins and other growth factors), serum albumin or replacements thereof, one or more carbohydrates (glucose, galactose, fructose, mannose, ribose, glycolytic metabolites), one or more antibiotics and/or antimycotics (e.g., penicillin, streptomycin, Fungizone), and one or more lipids (e.g., free and protein-bound fatty acids, triglycerides, phospholipids, cholesterol, ethanolamine). An exemplary supplement comprises N-2 (N2) supplement. Many commercialized serum replacement additives, such as KnockOut Serum Replacement (KOSR), N2, B27, StemPro (sometimes referred to herein as Stempro), Insulin-Transferrin-Selenium Supplement (ITS), and G5 are well known and are readily available to those skilled in the art. These additives are characterized by well-defined ingredients, so the concentrations of its components can be determined based on its proportion in the medium. In some embodiments, the culture medium comprises human epidermal growth factor (EGF), and basic fibroblast growth factor (bFGF).

By way of non-limiting example, the cells and/or small cellular clusters are cultured in a sterile environment containing serum-free media or serum-containing media, and antibiotics and antifungals or no antibiotics or anti-fungals, for no more than about 1, 2, 3, 4, 5, 6, 7, 8, 9 or 10 or more passages. The cells and/or and small cellular clusters are cultured in a basal culture media (e.g., Dulbecco's Modified Eagle Medium: Nutrient Mixture F-12™ (DMEM/F12™) media or an ADVANCED DMEM/F12™ media (Gibco-Invitrogen-Life Technologies, Carlsbad Calif.)) or an ULTRACULTURE™ media (BioWhittaker-Lonza Walkersville, Inc., Walkersville, Md.), optionally together with N2 supplement (Invitrogen) or B27 or B27 Xeno Free (Invitrogen), L-glutamine or GlutaMax or GlutaMAX-I (Invitrogen), and human recombinant growth factors including, for example, of EGF and bFGF (Invitrogen), or other growth factors. For example, the DMEM/F12™ media is used for human cells and the ULTRACULTURE™ media is used for feline or canine cells.

In some embodiments, cells and/or cell clusters are cultured for at least 1, 2, 3, 4, or 5 passages. In some embodiments, cells and/or cell clusters are cultured for more than 5 passages. In some embodiments, the culture medium comprises Dulbecco's Modified Eagle Medium DMEM/F12, Advanced DMEM/F12, Knockout DMEM/F12, Neurobasal media, ReNcell and Ultraculture media. In some embodiments, the culture medium comprises Advanced DMEM/F12.

In some embodiments, the culture medium comprises Advanced DMEM/F12, N-2 Supplement, GlutaMAX I, recombinant human epidermal growth factor (EGF), and basic fibroblast growth factor (bFGF). In some embodiments, the culture medium further comprises B27, B27 xeno-free, or StemPro. In some embodiments, the culture medium comprises Gentamicin at a concentration of about 30 μg/mL.

The culture media can also optionally be supplemented with albumin, or human or feline or canine albumin, or recombinant albumin, or albumin. By way of non-limiting example, albumin can be added in an amount to have an initial concentration of about 1.0 mg/ml.

Cultures of mammalian retinal progenitor cells can be produced in medium containing reduced serum or no serum. Examples of serum include fetal bovine serum, calf serum, newborn calf serum, goat serum, horse serum, human serum, rabbit serum, rat serum, mouse serum, among others. Under certain culture conditions, serum concentrations can range from about 0.05% v/v to about 20% v/v (e.g., 0.05, 0.10, 0.15, 0.20, 0.25, 0.30, 0.35, 0.40, 0.45, 0.50, 0.55, 0.60, 0.65, 0.70, 0.75, 0.80, 0.85, 0.90, 1, 1.5, 2, 2.5, 3, 3.5, 5, 4.5, 5, 5.5, 6, 6.5, 7, 7.5, 8, 8.5, 9, 9.5, 10, 10.5, 11, 11.5, 12, 12.5, 13, 13.5, 14, 14.5, 15, 15.5, 16, 16.5, 17, 17.5, 18, 18.5, 19, 19.5, or 20%). For example, in some differentiation processes, the serum concentration of the medium can be less than about 0.05% (v/v), less than about 0.1% (v/v), less than about 0.2% (v/v), less than about 0.3% (v/v), less than about 0.4% (v/v), less than about 0.5% (v/v), less than about 0.6% (v/v), less than about 0.7% (v/v), less than about 0.8% (v/v), less than about 0.9% (v/v), less than about 1% (v/v), less than about 2% (v/v), less than about 3% (v/v), less than about 4% (v/v), less than about 5% (v/v), less than about 6% (v/v), less than about 7% (v/v), less than about 8% (v/v), less than about 9% (v/v), less than about 10% (v/v), less than about 15% (v/v) or less than about 20% (v/v). In some embodiments, retinal progenitor cells and cell populations including retinal progenitor cells are grown without serum ("serum-free"), without serum replacement and/or without any supplement.

Retinal progenitor cells or cell populations containing retinal progenitor cells are cultured under "xeno-free" conditions. "Xeno-free" or "xenogen-free" refers to conditions where cells of a certain species (e.g., human cells) are grown or cultured only in the presence of human products or supplements (e.g., human serum albumin, human serum), but not products from other species. This is particularly important for cells that are used for transplantation into a human. Cells that have been exposed to a variety of undefined animal-derived products make them undesirable for clinical applications, because of an increased risk of graft rejection, immunoreactions, and viral or bacterial infections, prions, and yet unidentified zoonoses. Moreover, for all mammalian uses, including human use or non-human mammalian uses (e.g., veterinary uses), cells are screened for normal karyotype or presence of infection or contamination, e.g., by mycoplasma, gram negative bacteria (e.g., endotoxin test), fungi and the like. Cells may also be screened for tumorigenicity or transformation to a cancerous phenotype by telomerase activity assay, hTERT gene expression, and growth in soft agar or tumor formation in nude mice. Such assays are known in the art and well within the purview of the skilled artisan.

Retinal progenitor cells or cell populations containing retinal progenitor cells may be cultured on feeder cell layers (e.g., embryonic or adult fibroblasts), or in the presence of an extracellular matrix scaffold or substrates such as collagen, entactin, heparin sulfate proteoglycans, fibronectin, laminin, gelatin, or Matrigel. For example, PURECOL® collagen is known as the standard of all collagens for purity (>99.9% collagen content), functionality, and the most native-like collagen available. PURECOL® collagen is approximately 97% Type I collagen with the remainder being comprised of Type III collagen, and is ideal for coating of surfaces, providing preparation of thin layers for culturing cells, or use as a solid gel. Another example of a scaffold or substrate known in the art is CELLstart (Invitrogen).

In some embodiments, cell culture conditions can involve growth of cells in an incubator set at 37° C., 5% $CO_2$. Primary retinal cells, retinal progenitor cells or cell populations containing same may be cultured under normoxic or atmospheric conditions (about 20% $O_2$), and can also be grown under conditions that approximate oxygen levels of a developing fetal retina during gestation, i.e., "low" or "hypoxic" conditions, e.g., 0.5%, 1%, 1.5%, 2%, 2.5%, 3%, 3.5%, 4%, 4.5%, 5%, 5.5%, 6%, 6.5%, 7%, 7.5%, 8%, 8.5%, 9%, 9.5%, or 10% oxygen, or any increment in between. In some embodiments, cell culture conditions can involve growth of cells in an incubator set at: (1) 37° C., under 0 to 30% $CO_2$, and 0 to 50% $O_2$, (2) 37° C., less than or equal to 5% $CO_2$ and less than or equal to 20% $O_2$; or (3) 37° C., less than or equal to 5% $CO_2$ and less than or equal to 3% $O_2$.

Plating density refers to the number of cells per volume of culture medium or the number of cells per cm2 in adherent culture. A similar term in this context is "confluence", which is commonly used as a measure of the number of the cells in a cell culture dish or a flask, and refers to the coverage of the dish or the flask by the cells. For example, 100 percent confluency means the dish is completely covered by the cells, and therefore no more room left for the cells to grow; whereas 50 percent confluency means roughly half of the dish is covered and there is still room for cells to grow.

In some embodiments, the methods comprise a first passage, the first passage comprising seeding culture flasks or plates with cells at a density of about $0.5 \times 10^6$ to about $3.0 \times 10^6$ cells per square centimeter (cm²), about $0.5 \times 10^6$ to about $5.0 \times 10^6$ cells/cm², about $0.55 \times 10^6$ to about $4.0 \times 10^6$ cells/cm², about $0.55 \times 10^6$ to about $3.0 \times 10^6$ cells/cm², $0.55 \times 10^6$ to about $2.5 \times 10^6$ cells/cm² or about $0.55 \times 10^6$ to about $2.1 \times 10^6$ cells/cm². In some embodiments, the first passage comprises seeding the culture flasks or plates with cells at a density of about $0.5 \times 10^6$ to about $3.0 \times 10^6$ cells/cm². In some embodiments, the first passage comprises seeding the culture flasks or plates with cells at a density of about $0.59 \times 10^6$ to about $2.29 \times 10^6$ cells/cm².

In some embodiments, the methods comprise a second passage, the second passage comprising seeding culture flasks or plates with cells at a density of about $0.05 \times 10^6$ to about $1 \times 10^6$ cells/cm², about $0.07 \times 10^6$ to about $0.80 \times 10^6$ cells/cm², about $0.10 \times 10^6$ to about $0.5 \times 10^6$ cells/cm², about $0 \ldots 10 \times 10^6$ to about $0.4 \times 10^6$ cells/cm², about $0.13 \times 10^6$ to about $0.35 \times 10^6$ cells/cm², or about $0.14 \times 10^6$ to about $0.32 \times 10^6$ cells/cm². In some embodiments, the second passage comprises seeding the culture flasks or plates with cells at a density of about $0.1 \times 10^6$ to about $0.5 \times 10^6$ cells/cm². In some embodiments, the second passage comprises seeding the culture flasks or plates with cells at a density of about $0.14 \times 10^6$ to about $0.43 \times 10^6$ cells/cm².

In some embodiments, the methods comprise a third passage, the third passage comprising seeding culture flasks or plates with cells at a density of about $0.01 \times 10^6$ to about $0.5 \times 10^6$ cells/cm², about $0.02 \times 10^6$ to about $0.45 \times 10^6$ cells/cm², about $0.03 \times 10^6$ to about $0.40 \times 10^6$ cells/cm², about $0.04 \times 10^6$ to about $0.30 \times 10^6$ cells/cm², about $0.05 \times 10^6$ to about $0.20 \times 10^6$ cells/cm² or about $0.05 \times 10^6$ to about $0.10 \times 10^6$ cells/cm². In some embodiments, the third passage comprises seeding the culture flasks or plates with cells at a density of about $0.03 \times 10^6$ to about $0.2 \times 10^6$ cells/cm². In some embodiments, the third passage comprises seeding the culture flasks or plates with cells at a density of about $0.05 \times 10^6$ to about $0.1 \times 10^6$ cells/cm².

In some embodiments, the methods comprise a fourth and optionally, further passages, the fourth and further passages comprising seeding culture flasks or plates with cells at a density of about 10,000 to about 60,000 cells/cm², about 10,000 to about 50,000 cells/cm², about 10,000 to about 40,000 cells/cm², about 20,000 to about 60,000 cells/cm², about 20,000 to about 50,000 cells/cm², or about 20,000 to about 40,000 cells/cm². In some embodiments, the fourth passage comprises seeding the culture flasks or plates with cells at a density of about 10,000 to about 60,000 cells/cm². In some embodiments, the fourth passage comprises seeding the culture flasks or plates with cells at a density of about 20,000 to about 40,000 cells/cm².

In some embodiments, the methods comprise seeding culture flasks with cells at higher densities at earlier passages and lower densities at later passages. Without wishing to be bound by theory, it is thought that during the first several passages cells are transformed from cell clusters to single cells, and this gradual transformation from clusters to cells contributes to the increased cell viability of the methods described herein. Later passages are seeded as single cells, and seeding density drops rapidly, and then becomes consistent. As a non-limiting example, cells are seeded in culture flasks or plates at a density of about $0.5 \times 10^6$ to about $3.0 \times 10^6$ cells/cm² at the first passage, about $0.1 \times 10^6$ to about $0.5 \times 10^6$ cells/cm² at the second passage, about $0.03 \times 10^6$ to about $0.2 \times 10^6$ cells/cm² at the third passage, and about 10,000 to about 60,000 cells/cm² at a fourth and further passages. As a further non-limiting example, cells are seeded in culture flasks or plates at a density of about $0.59 \times 10^6$ to about $2.29 \times 10^6$ cells/cm² at the first passage, about $0.14 \times 10^6$ to about $0.32 \times 10^6$ cells/cm² at the second passage, about $0.05 \times 10^6$ to about $0.1 \times 10^6$ cells/cm² at the third passage, and about 20,000 to about 40,000 cells/cm² at a fourth and further passages.

In some embodiments, the period of time between immediately sequential passages is between is 2 to 8 days, 3 to 6 days, 4 to 5 days or 3 to 4 days. In some embodiments, the period of time between passages is 4 days. In some embodiments, the period of time between immediately sequential passages is 3 days.

In some embodiments, the passaging protocol comprises target thresholds for the numbers of viable cells, and cell culture is terminated if these target thresholds are not met. For example, cell culture may be terminated at the end of passage 3 (P3) if less than 90 million, 100 million, 110 million, 120 million, 130 million, 140 million or 150 million viable cells are produced. As a further example, cell culture may be terminated at the end of passage 4 (P4) if less than 200 million, less than 250 million, less than 300 million, less than 350 million, less than 400 million, less than 450 million or less than 500 million viable cells are produced.

Passaging (also known as subculture or splitting cells) involves transferring a small number of cells into a new vessel. Cells can be cultured for a longer time if they are split regularly, as it avoids the senescence associated with prolonged high cell density. Suspension cultures are easily passaged with a small amount of culture containing a few cells diluted in a larger volume of fresh media. For adherent cultures, cells first need to be detached. This is commonly done with a mixture of an enzyme such as trypsin-EDTA or a trypsin equivalent and EDTA, or non-enzymatic solution like Cell Dissociation Buffer; however, a variety of enzyme or non-enzyme mixes or preparations are available for this purpose. A small number of detached cells can then be used to seed a new culture.

In some embodiments, cells are treated with a solution comprising trypsin or equivalent that differs at the first, second and third passages. In an exemplary protocol, cells are treated with a first enzymatic solution comprising TrypLE and Ethylenediamine tetraacetic acid (EDTA) at a ratio of 1:4 at the first passage, a second enzymatic solution comprising TrypLE, EDTA and Dulbecco's phosphate buffered saline (DPBS) at a ratio of 1:1:3 at the second passage, and a third enzymatic solution comprising TrypLE and DPBS at a ratio of 1:1 at the third and every subsequent passage. In a further exemplary protocol, cells are treated with a first enzymatic solution comprising TrypLE, EDTA and PBS at a ratio of 1:1:3 at the first passage, a second enzymatic solution comprising TrypLE and DPBS at a ratio of 1:1 at the second passage, and a third enzymatic solution comprising TrypLE and DPBS at a ratio of 1:1 at the third and every subsequent passage. Cells can be treated with trypsin or equivalent solutions for between about 5-20 minutes, about 6-10 minutes, about 5-10 minutes, about 7-8 minutes, or about 5-7 minutes. Cell viability, number and/or morphology can be determined at any passage. For example, cell viability and number can be determined at passages 3 and 4 to decide whether or not to terminate cell culture, or to determine cell seeding density. Most primary cell cultures have limited lifespan and do not proliferate indefinitely. After a certain number of population doublings (called the Hayflick limit), cells undergo the process of senescence and stop dividing, while generally retaining viability. In some embodiments, the retinal progenitor cells and cell populations can be cultured for no more than 10 passages, for example, are passaged one, two, three, four, five, six, seven, eight, nine, or ten passages. In some embodiments, the RPCs are passaged about 4-6 (e.g., 4, 5, or 6) times under standard oxygen conditions and, optionally, subsequently cultured for about 1-10 (e.g., 1, 2, 3, 4, 5, 6, 7, 8, 9, or 10) passages under low oxygen conditions.

In alternative embodiments, cells can be passaged (in standard oxygen conditions, in low oxygen conditions, and/or in any combinations thereof) more than 5 times, such as, e.g., six, seven, eight, nine, ten, eleven, twelve, thirteen, fourteen, fifteen, sixteen, seventeen, eighteen, nineteen, twenty or more passages. In certain embodiments, the retinal progenitor cells and cell populations are cultured for about 5-32 (e.g., 5, 6, 7, 8, 9, 10, 11, 12, 13, 14, 15, 16, 17, 18, 19, 20, 21, 22, 23, 24, 25, 26, 27, 28, 29, 30, 31 or 32) passages. Those skilled in the art will recognize that other methods known in the art may be used to culture the cells for more than 32 passages (i.e., 33, 34, 35, 36, 37, 38, 39, 40, 41, 42, 43, 44, 45, 46, 47, 48, 49, 50, or more passages).

Any suitable container such as flask, plate or cell stack may be used to passage cells using the methods described herein. Exemplary flasks include T25 and T75 flasks. Cell-Stacks (CS) are stacked culture chambers available, for example, from Corning. In some embodiments, the flask, plate or cell stack may be coated. Flasks, plates and cell stacks may be coated with fibronectin, ornithine, poly-lysine or laminin, diluted in Dulbecco's Phosphate-Buffered Saline (DPBS). In some embodiments, flasks, plates or cell stacks are coated with fibronectin. In some embodiments, the fibronectin is xeno free. Optionally, the flask, plate or cell stack may be rinsed with culture medium before placing the cells therein.

In various embodiments, the sample of cells is screened for the presence of a pathogen, a bacteria, an endotoxin, a fungus, a mycoplasma, a virus, a hepatitis virus or an HIV virus. The sample of cells can also be screened for the presence of a normal karyotype; viability; and/or tumorigenicity. Optionally, the sample of cells does not exhibit elevated telomerase activity.

In any of these methods, retinal cells and/or retinal tissue can be frozen either before or after isolation, selection, and/or culture. Cell freezing can be accomplished using any cryopreservation agents and/or techniques commonly used in the art. Frozen cells can be thawed prior to use using any protocol known in the art.

The viability of cells can be examined prior to their use in any of the methods described herein. In alternative embodiments, by way of non-limiting examples, prior to cryo-preservation, at least 70% (e.g., 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100%) of the cells are viable. Following thawing, in alternative embodiments, at least 70% (e.g., 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100%) of the cells are viable. Similarly, upon cell culture recovery, in alternative embodiments at least 70% (e.g., 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100%) of the cells are viable. Determination of the number of viable cells at any stage is within the routine level of skill in the art.

Accordingly, the disclosure provides methods of cryopreserving a plurality of retinal progenitor cells produced using the isolation and culture methods described herein. In some embodiments, the methods comprise (i) enzymatically dissociating the cells using trypsin or equivalent, (ii) halting the dissociation with an excess of the culture medium or Advanced DMEM/F12, (iii) centrifuging the cells via centrifugation at between 10×g and 10,000×g for 1 to 30 minutes, (iv) resuspending the cells in culture medium and determining the total cell count and viability, (v) adding cryopreservation medium to achieve a final dimethylsulfoxide (DMSO) concentration of between 5 and 30%, (vi) aliquoting a plurality of cells into each cryovial, (vii) freezing each vial by using a Control Rate Freezer, and (viii) placing each vial of cells in liquid $N_2$. Any suitable freezing method known in the art may be used. For example, cells may be frozen using a Cryo 1C freezing container placed in a −80° C. freezer. In some embodiments, the trypsin equivalent is TrypLE, such as TrypLE Express or TrypLE Select (ThermoFisher, or Invitrogen, e.g.). In some embodiments, the cryopreservation medium comprises culture medium and 20% DMSO. In some embodiments, the cryopreservation medium is added to the cells and cell culture medium at a ratio of 1:1 to achieve a final concentration of 10% DMSO. In some embodiments, plurality of retinal progenitor cells is aliquoted and frozen at about $0.5 \times 10^6$ to $50 \times 10^6$ cells per cryovial. In some embodiments, the plurality of retinal progenitor cells is aliquoted and frozen at about $0.5 \times 10^6$ to about $40 \times 10^6$ cells per mL of medium (e.g. culture medium plus 10% DMSO), about $0.5 \times 10^6$ to about $20 \times 10^6$ cells/mL of medium, about $0.5 \times 10^6$ to about $10 \times 10^6$ cells/mL of medium, about $1 \times 10^6$ to about $40 \times 10^6$ cells per mL of medium, about $1 \times 10^6$ to about $20 \times 10^6$ cells/mL of medium, about $1 \times 10^6$ to about $10 \times 10^6$ cells/mL of medium, about $10 \times 10^6$ to about $30 \times 10^6$ cells/mL of medium, about $10 \times 10^6$ to about $20 \times 10^6$ cells/mL of medium, about $2 \times 10^6$ to about $10 \times 10^6$ cells/mL of medium, about $2 \times 10^6$ to about $8 \times 10^6$ cells/mL of medium, or about $2 \times 10^6$ to about $5 \times 10^6$ cells/mL of medium. In some embodiments, the plurality of retinal progenitor cells is aliquoted and frozen at about $0.5 \times 10^6$ to about $20 \times 10^6$ cells/mL of medium. In some embodiments, the plurality of retinal progenitor cells is aliquoted and frozen at about $2 \times 10^6$ to about $8 \times 10^6$ cells/mL of medium. In some embodiments, the plurality of retinal progenitor cells is aliquoted and frozen at about $10 \times 10^6$ cells/mL of medium. In some embodiments, a cryovial contains about 1 mL, about 2 mL, about 3 mL, about 4 mL, about 5 mL, about 6 mL, about 7 mL, about 8 mL, about 9 mL or about 10 mL of cryopreservation medium (e.g., culture medium plus DMSO) and retinal progenitor cells. In some embodiments, a cryovial contains about 1 mL of medium and retinal progenitor cells. In some embodiments, a cryovial contains about 5 mL of medium and retinal progenitor cells.

In certain embodiments, the final product formulation has been shown to retain optimal viability (e.g., at least 85%) for up to 4 hours or more (e.g., 4, 5, 6, 7, 8, 9, 10, 11, 12, 13, 14, 15, 16, 17, 18, 19, 20, 21, 22, 23, 24, or more) when kept on ice (e.g., at 0-4° C.). This, in turn, will allow local transportation of the cell preparation to regional clinical sites.

Further expansion of cells under low oxygen conditions can be used to greatly enhance the cell yield per donation. For example, in some embodiments, cells may be passaged 5-12 (i.e., 5, 6, 7, 8, 9, 10, 11 or 12) or more times total. By way of non-limiting example, in one embodiment, this may include a secondary low oxygen expansion of 3-6 passages (i.e., 3, 4, 5, or 6) that occurs after 4-6 passages (i.e., 4, 5, or 6) in standard oxygen conditions. However, those skilled in the art will recognize that the total number of passages may be about 1-32 or more passages (e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32 or more), and this may include a secondary low oxygen expansion of 1-20 or more passages (e.g., 1, 2, 3, 4, 5, 6, 7, 8, 9, 10, 11, 12, 13, 14, 15, 16, 17, 18, 19, or 20 or more). Determination of the appropriate number of total passages as well as the number of low oxygen passages is within the routine level of skill in the art. Use of this secondary low oxygen culture passages greatly expand yield from a working bank of hRPCs (such as those that have are derived by culturing under standard oxygen conditions). For example, cells from the standard normal oxygen bank can be thawed and further expanded for an additional 1-20 (e.g., 1, 2, 3, 4, 5, 6, 7, 8, 9, 10, 11, 12, 13, 14, 15, 16, 17, 18, 19, or 20) passages under low oxygen conditions.

While the use of fewer low oxygen cell passages is possible, the resulting yield would likely be lower. Moreover, while the use of more low oxygen cell passages is also possible, this would potentially have an increased risk of the resulting product being faulty due to potential phenotypic drift with loss of efficacy and/or accumulation of undesired genetic abnormalities.

Following the secondary low oxygen culture passages, in some embodiments, the retinal progenitor cells undergo a "recovery period" in which they are allowed to grow under standard oxygen conditions for a short period of time between 1 hour and up to 5 days (i.e., 1, 2, 3, 4, 5, 6, 7, 8, 9, 10, 11, 12, 13, 14, 15, 16, 17, 18, 19, 20, 21, 22, 23, 24, 24, 36, 48, 60, 72, 84, 96, 108, or 120 hours). In alternative embodiments, during this recovery period, the cells are allowed to growth without undergoing any further passaging.

Accordingly, in one non-limiting example, retinal progenitor cells for use in any of the compositions and methods described herein may be produced using a "hybrid" approach involving (a) culture under standard oxygen conditions for a number of passages followed by (b) culture under low oxygen conditions for a number of passages, optionally followed by (c) culture under standard oxygen conditions for a set period of time without any further passaging. Determination of the appropriate number passages under standard oxygen conditions and/or low oxygen conditions as well as the appropriate duration of the recovery period is within the routine level of skill in the art.

The resulting cell product produced using this new culture methodology has been tested in vitro and in animals, and results similar to those with cell product that did not undergo the secondary low oxygen culture have been observed.

Those skilled in the art will recognize that the addition of this secondary low oxygen component to the overall process is conducive to automated manufacturing methods in that complex procedures such as initial dissection and plating are not needed and the passaging done will be quite standardized with cells that are strongly proliferating.

RPCs can additionally be generated through induced pluripotent stem cell (iPS) conversion of existing RPCs followed by expansion in a more primitive, proliferative state. The iPS can then be re-differentiation back to RPCs using any method(s) known in the art. In this scenario, the previous epigenetic imprinting conferred as RPCs helps to redirect the cells back to their original state, thereby increasing RPC yield and/or promoting safety of a high yield allogeneic product (i.e., by avoiding contamination with pluripotent cells). This expansion methodology could provide a very large and potentially infinite (non-senescing) source of RPCs, derived from clinically proven RPC samples, without the need for repeated fetal tissue procurement.

RPCs can additionally be manufactured from a pluripotent cell line, either one such line derived from RPCs, as above, or not. Such a derivation could include partial differentiation into "embryoid bodies" containing primitive retinal structures, i.e., eye cup derivatives, from which RPCs could be harvested, purified, and further expanded.

Similar methods could be performed using autologous cells where donor cells for iPS are obtained from ciliary body epithelium or from iris, as both of these tissues are accessible to the surgeon and have developmental imprinting that overlaps with (although not exactly the same as) the retina.

Compositions and Formulations

The retinal progenitor cells and cell populations described herein may be formulated as a composition for administration by any or a variety of means including orally, parenterally, by inhalation spray, nasally, topically, intrathecally, intrathecally, intracerebrally, epidurally, intracranially or rectally. Compositions and formulations disclosed herein can contain pharmaceutically or veterinarily acceptable liquids, carriers, adjuvants and vehicles and can be in the form of liquids, tablets, capsules, implants, aerosols, gels, liposomes, nanoparticles and the like.

The retinal progenitor cells and cell populations may be administered to a subject in the form of pharmaceutical or veterinary compositions. The phrase "pharmaceutically acceptable" refers to molecular entities and compositions that do not produce adverse, allergic, or other untoward reactions when administered to an animal or a human. As used herein, "pharmaceutically acceptable carrier" includes any and all aqueous and nonaqueous carriers which includes water, ethanol, polyols (such as glycerol, propylene glycol, polyethylene glycol, and the like), and suitable mixtures thereof, vegetable oils, such as olive oil, and injectable organic esters, such as ethyl oleate.

The pharmaceutically acceptable carrier may optionally include albumin (e.g., human albumin), which is a protein that could improve cell survival within the preparation.

Likewise, any of the compositions or preparations disclosed herein may also include the excipient HypoThermosol®-FRS (HTS-FRS) (BioLife Solutions, Inc.), which is commercially-available hypothermic storage solution/formulation designed to mediate the level of post-storage necrosis and apoptosis in cells undergoing prolonged periods of hypothermic (2° C.-10° C.) preservation. (See, e.g., U.S. Pat. Nos. 6,921,633; 6,632,666; and WO 2005/009766).

The addition of albumin and/or HTS could be used to extend the viability time for the retinal progenitor cells within any of the preparations disclosed herein up to about 24 hours (i.e., about 1, 2, 3, 4, 5, 6, 7, 8, 9, 10, 11, 12, 13, 14, 15, 16, 17, 18, 19, 20, 21, 22, 23, or 24 hours).

Proper fluidity can be maintained, for example, by the use of coating materials, such as lecithin, by the maintenance of the required particle size in the case of dispersions, and by the use of surfactants. These compositions may also contain adjuvants such as preservatives, wetting agents, emulsifying agents and dispersing agents. Prevention of the presence of microorganisms may be ensured both by sterilization procedures and by the inclusion of various antibacterial and antifungal agents, for example, paraben, chlorobutanol, sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption such as aluminum monostearate and gelatin. It must be stable under the conditions of manufacture and storage and must be preserved against the contaminating action of microorganisms, such as bacteria and fungi. The use of such media and agents for pharmaceutically active substances is well known in the art.

An effective amount of the retinal progenitor cells or cell populations must be administered to the subject. An "effective amount" or "therapeutically effective amount" refers to the amount of the composition that produces a desired effect. An effective amount will depend, for example, in part, upon the molecule or agent delivered (here the retinal progenitor cells or cell populations), the indication for which the therapeutic agent is being used, the route of administration, and the size (body weight, body surface or organ size) and condition (the age and general health) of the subject or patient. Accordingly, the clinician or physician may titer the dosage and modify the route of administration to obtain the optimal therapeutic effect. An effective amount of a particular agent for a specific purpose can be determined using methods well known to those in the art. For any composition defined herein, the effective amount can be estimated initially either in cell culture assays or in animal models such as mice, rats, rabbits, dogs, pigs, or monkeys. An animal model may also be used to determine the appropriate concentration range and route of administration.

Such information can then be used to determine useful doses and routes for administration in humans.

Examples of effective amounts of the compositions described herein include cell suspensions at a volume of 5 µl, 10 µl, 15 µl, 20 µl, 25 µl, 50 µl, 100 µl, 150 µl, 200 µl, 250 µl, 300 µl, 350 µl, 400 µl, 450 µl, 500 µl or any increment in between up to 5000 µl (5 ml) (e.g., 500, 550, 600, 650, 700, 750, 800, 850, 900, 950, 1000, 1050, 1100, 1150, 1200, 1250, 1300, 1350, 1400, 1450, 1500, 1550, 1600, 1650, 1700, 1750, 1800, 1850, 1900, 1950, 2000, 2050, 2100, 2150, 2200, 2250, 2300, 2350, 2400, 2450, 2500, 2550, 2600, 2650, 2700, 2750, 2800, 2850, 2900, 2950, 3000, 3050, 3100, 3150, 3200, 3250, 3300, 3350, 3400, 3450, 3500, 3550, 3600, 3650, 3700, 3750, 3800, 3850, 3900, 3950, 4000, 4050, 4100, 4150, 4200, 4250, 4300, 4350, 4400, 4450, 4500, 4550, 4600, 4650, 4700, 4750, 4800, 4850, 4900, 4950, or 5000 µl).

The lower and upper volume limits are limited by the delivery system and/or method. See, e.g., Kayikcuiglu, O. R. et al, (2006) Retina 26(9): 1089-90. For example, the upper volume limit when administered without vitrectomy is approximately 200 µl due to increased intraocular pressure. The upper volume limit when administered with vitrectomy into the vitreous cavity is limited by the volume of the vitreous cavity and can contain up to 5 ml or more. The upper limit for subretinal injection may be up to 200 µl due to retinal detachment. In alternative embodiments, these volumes include anywhere between 1000 to 10 million cells per dose, or 1000 to 2000 cells per dose, 2000 to 3000 cells per dose, 3000 to 4000 cells per dose, 400 to 5000 cells per dose, 5000 to 6000 cells per dose, 6000 to 7000 cells per dose, 7000 to 8000 cells per dose, 8000 to 9000 cells per dose, 9000 to 10,000 cells per dose, 10,000 to 15,000 cells per dose, 15,000 to 20,000 cells per dose, 20,000 to 25,000 cells per dose, 25,000 to 30,000 cells per dose, 30,000 to 35,000 cells per dose, 35,000 to 40,000 cells per dose, 40,000 to 45,000 cells per dose, 45,000 to 50,000 cells per dose, 50,000 to 55,000 cells per dose, 55,000 to 60,000 cells per dose, 60,000 to 65,000 cells per dose, 65,000 to 70,000 cells per dose, 70,000 to 75,000 cells per dose, 75,000 to 80,000 cells per dose, 80,000 to 85,000 cells per dose, 85,000 to 90,000 cells per dose, 90,000 to 95,000 cells per dose, 95,000 to 100,000 cells per dose, 100,000 to 125,000 cells per dose, 125,000 to 150,000 cells per dose, 150,000 to 200,000 cells per dose, 200,000 to 250,000 cells per dose, 250,000 to 300,000 cells per dose, 300,000 to 350,000 cells per dose, 350,000 to 400,000 cells per dose, 400,000 to 450,000 cells per dose, 450,000 to 500,000 cells per dose, 500,000 to 550,000 cells per dose, 550,000 to 600,000 cells per dose, 600,000 to 650,000 cells per dose, 650,000 to 700,000 cells per dose, 700,000 to 750,000 cells per dose, 750,000 to 800,000 cells per dose, 800,000 to 850,000 cells per dose, 850,000 to 900,000 cells per dose, 900,000 to 950,000 cells per dose, 950,000 to 1,000,000 cells per dose or in any increment in between 1000 cells and up to 10 million cells per dose. Dosages may, of course, vary according to frequency and duration of administration. In alternative embodiments the dosage of cells in the compositions described herein contains a high number of cells in a small, volume, such as, for example, 0.5 million cells per 100 µl. Cell numbers may be counted by any method known in the art, such as by hemacytometer, spectrophotometry, Coulter counter, flow cytometry, etc. Dosing may be administered once or may be administered over the course of several treatments.

Compositions can also be formulated for parenteral administration into the eye (particularly into the vitreous cavity or subretinal space), a vitreous cavity or a subretinal space, retina, brain, nerve or CNS by transscleral delivery, or by any method or protocol known in the art, e.g., including a transscleral delivery as described in U.S. Pat. No. 7,585, 517; a sustained release delivery device for delivery to the interior of a patient's eye as described in U.S. Pat. No. 7,883,717; a device for insertion in the vitreous region of the eye as described in U.S. Pat. No. 5,378,475 or 5,466,233; or by use of a hypodermic syringe or angled insertion pathway, e.g., as described in U.S. Patent Application Publication Nos. 20110112470 or 20100256597 (describing a microneedle for targeted administration to a patient's eye); or via a hydrophilic polymer hydrogel with dimensions to pass through a puncta lacrimali e.g., as described in U.S. Patent Application Publication No. 20100209478; or a device that provides access to the sub-retinal space in a human eye e.g., as described in U.S. Patent Application Publication No. 20100191176. Anterior chamber paracentesis also can be performed as determined by one of skill in the art. Methods do not require suturing of globe during and/or after a procedure, particularly for intravitreal placement. However, this may be necessary for methods utilizing a vitrectomy procedure, for example, when placing cells in the subretinal space.

The compositions disclosed herein may also be formulated for intrathecal, intracerebral epidural, subcutaneous, intravenous, intramuscular and/or intraarterial administration; e.g., as described in U.S. Patent Application Publication No. 200500480021; by injection routes but also including a variety of infusion techniques. Administration may be carried out through the use of catheters or pumps, e.g., an intrathecal pump, or an implantable medical device. In alternative embodiments methods also may involve administration or transplantation of implants and artificial organs, bioreactor systems, cell culture systems, plates, dishes, tubes, bottles and flasks and the like, containing the retinal progenitor cells, cell populations, or compositions disclosed herein, such as those described in U.S. Pat. Nos. 7,388,042; 7,381,418; 7,379,765; 7,361,332; 7,351,423; 6,886,568; 5,270,192; and U.S. Patent Application Publication Nos. 20040127987; 20080119909; 20080118549; 20080020015; 20070254005; 20070059335; 20060128015.

The compositions containing retinal progenitor cells or cell populations may optionally be co-administered with one or more drugs. Non-limiting examples of drugs may include anti-angiogenesis agents such as angiostatin, anecortave acetate, thrombospondin, VEGF receptor tyrosine kinase inhibitors and anti-vascular endothelial growth factor (anti-VEGF) drugs such as ranibizumab and bevacizumab, pegaptanib, sunitinib and sorafenib and any of a variety of known small-molecule and transcription inhibitors having anti-angiogenesis effect; classes of known ophthalmic drugs, including: glaucoma agents, such as adrenergic antagonists, including for example beta-blocker agents such as acebutolol, atenolol, bisoprolol, carvedilol, asmolol, labetalol, nadolol, penbutolol, pindolol, propranolol, metipranolol, betaxolol, carteolol, levobetaxolol, levobunolol and timolol; adrenergic agonists or sympathomimetic agents such as epinephrine, dipivefrin, clonidine, aparclonidine, and brimonidine; parasympathomimetics or cholingeric agonists such as pilocarpine, carbachol, phospholine iodine, and physostigmine, salicylate, acetylcholine chloride, eserine, diisopropyl fluorophosphate, demecarium bromide); muscarinics; carbonic anhydrase inhibitor agents, including topical and/or systemic agents, for example acetozolamide, brinzolamide, dorzolamide and methazolamide, ethoxzolamide, diamox, and dichlorphenamide; mydriatic-cycloplegic agents such as atropine, cyclopentolate, succinylcholine, homatropine, phenylephrine, scopolamine and tropicamide; prostaglandins such as prostaglandin F2 alpha, antiprostaglandins, prostaglandin precursors, or prostaglandin analog agents such as bimatoprost, latanoprost, travoprost and/or unoprostone.

Other examples of drugs may also include, but are not limited to, anti-inflammatory agents including for example glucocorticoids and corticosteroids such as betamethasone, cortisone, dexamethasone, dexamethasone 21-phosphate, methylprednisolone, prednisolone 21-phosphate, prednisolone acetate, prednisolone, fluoromethalone, loteprednol, medrysone, fluocinolone acetonide, triamcinolone acetonide, triamcinolone, triamcinolone acetonide, beclomethasone, budesonide, flunisolide, fluorometholone, fluticasone, fludrocortisone, hydrocortisone, hydrocortisone acetate, loteprednol, rimexolone and non-steroidal anti-inflammatory agents including, for example, aspirin, diclofenac, flurbiprofen, ibuprofen, bromfenac, nepafenac, and ketorolac, salicylate, indomethacin, naxopren, piroxicam and nabumetone diflunisal, etodolac, fenoprofen, flurbiprofen, indomethacine, ketoprofen, meclofenamate, mefenamic acid, meloxicam, nabumetone, oxaprozin, piroxicam, salsalate, sulindac and tolmetin; COX-2 inhibitors like celecoxib, rofecoxib and Valdecoxib; anti-infective or antimicrobial agents such as antibiotics including, for example, tetracycline, chlortetracycline, bacitracin, neomycin, polymyxin, gramicidin, cephalexin, oxytetracycline, chloramphenicol, rifampicin, ciprofloxacin, tobramycin, gentamycin, erythromycin, penicillin, sulfonamides, sulfadiazine, sulfacetamide, sulfamethizole, sulfisoxazole, nitrofurazone, sodium propionate, aminoglycosides such as gentamicin, tobramycin, amikacin and streptomycin; fluoroquinolones such as ciprofloxacin, gatifloxacin, levofloxacin, moxifloxacin, norfloxacin, ofloxacin; bacitracin, erythromycin, fusidic acid, neomycin, polymyxin B, gramicidin, trimethoprim and sulfacetamide; antifungals such as amphotericin B, caspofungin, clotrimazole, fluconazole, itraconazole, ketoconazole, voriconazole, terbinafine, nystatin and miconazole; anti-malarial agents such as chloroquine, atovaquone, mefloquine, primaquine, quinidine and quinine; anti-mycobacterium agents such as ethambutol, isoniazid, pyrazinamide, rifampin and rifabutin; and/or anti-parasitic agents such as albendazole, mebendazole, thiobendazole, metronidazole, pyrantel, atovaquone, iodoquinaol, ivermectin, paromycin, praziquantel, and trimatrexate.

Other examples of drugs may also include, but are not limited to, antiviral agents such as idoxuridine trifluorothymidine, acyclovir, cidofovir, famciclovir, gancyclovir, valacyclovir, valganciclovir, vidarabine, trifluridine and foscarnet; protease inhibitors such as ritonavir, saquinavir, lopinavir, indinavir, atazanavir, amprenavir and nelfinavir; nucleotide/nucleoside/non-nucleoside reverse transcriptase inhibitors such as abacavir, ddl, 3TC, d4T, ddC, tenofovir and emtricitabine, delavirdine, efavirenz and nevirapine; other antiviral agents such as interferons, ribavirin and trifluridiene; anti-bacterial agents, including cabapenems like ertapenem, imipenem and meropenem; cephalosporins such as cefadroxil, cefazolin, cefdinir, cefditoren, cephalexin, cefaclor, cefepime, cefoperazone, cefotaxime, cefotetan, cefoxitin, cefpodoxime, cefprozil, ceftaxidime, ceftibuten, ceftizoxime, ceftriaxone, cefuroxime and loracarbef; other macrolides and ketolides such as azithromycin, clarithromycin, dirithromycin and telithromycin; penicillins (with and without clavulanate) including amoxicillin, ampicillin, pivampicillin, dicloxacillin, nafcillin, oxacillin, piperacillin, and ticarcillin; tetracyclines such as doxycycline, minocycline and tetracycline; and/or other anti-bacterials such as aztreonam, chloramphenicol, clindamycin, linezolid, nitrofurantoin and vancomycin.

Other examples of drugs may also include, but are not limited to, immune-modulating agents such as antiallergenics, including, for example, sodium chromoglycate, antazoline, methapyriline, chlorpheniramine, cetrizine, pyrilamine, prophenpyridamine; aldesleukin, adalimumab, azathioprine, basiliximab, daclizumab, etanercept, hydroxychloroquine, infliximab, leflunomide, methotrexate, mycophenolate mofetil, and sulfasalazine; anti-histamine agents such as azelastine, emedastine, loratadine, desloratadine, cetirizine, diphenhydramine, chlorpheniramine, dexchlorpheniramine, clemastine, cyproheptadine, fexofenadine, hydroxyzine, promethazine and levocabastine; immunological drugs (such as vaccines and immune stimulants); MAST cell stabilizer agents such as cromolyn sodium, ketotifen, lodoxamide, nedocrimil, olopatadine and pemirolastciliary body ablative agents, such as gentimicin and cidofovir; and other ophthalmic agents such as verteporfin, proparacaine, tetracaine, cyclosporine and pilocarpine; inhibitors of cell-surface glycoprotein receptors; decongestants such as phenylephrine, naphazoline, tetrahydrazoline; lipids or hypotensive lipids; dopaminergic agonists and/or antagonists such as quinpirole, fenoldopam, and ibopamine; vasospasm inhibitors; vasodilators; antihypertensive agents; angiotensin converting enzyme (ACE) inhibitors; angiotensin-1 receptor antagonists such as olmesartan; microtubule inhibitors; molecular motor (dynein and/or kinesin) inhibitors; actin cytoskeleton regulatory agents such as cyctchalasin, latrunculin, swinholide A, ethacrynic acid, H-7, and Rho-kinase (ROCK) inhibitors; remodeling inhibitors; modulators of the extracellular matrix such as tert-butylhydro-quinolone and AL-3037A; adenosine receptor agonists and/or antagonists such as N-6-cylclophexyladenosine and (R)-phenylisopropyladenosine; serotonin agonists; hormonal agents such as estrogens, estradiol, progestational hormones, progesterone, insulin, calcitonin, parathyroid hormone, peptide and vasopressin hypothalamus releasing factor; growth factor antagonists or growth factors, including, for example, epidermal growth factor, fibroblast growth factor, platelet derived growth factor, transforming growth factor beta, somatotrapin, fibronectin, connective tissue growth factor, bone morphogenic proteins (BMPs), brain derived neurotrophic factor (BDNF), ciliary neurotrophic factor (CNTF), glial cell line-derived neurotrophic factor (GDNF), insulin-like growth factor (IGF), and nerve growth factor (NGF); and/or cytokines such as interleukins, CD44, cochlin, osteopontin, pleotrophin, midkine, vascular endothelial growth factor (VEGF), and serum amyloids, such as serum amyloid A.

Other therapeutic agents may include, but are not limited to, neuroprotective agents such as lubezole, nimodipine and related compounds, and including blood flow enhancers, sodium channels blockers, glutamate inhibitors such as memantine, neurotrophic factors, nitric oxide synthase inhibitors; free radical scavengers or anti-oxidants; chelating compounds; apoptosis-related protease inhibitors; compounds that reduce new protein synthesis; radiotherapeutic agents; photodynamic therapy agents; gene therapy agents; genetic modulators; and dry eye medications such as cyclosporine A, delmulcents, and sodium hyaluronate; alpha blocker agents such as doxazosin, prazosin and terazosin; calcium-channel blockers such as amlodipine, bepridil, diltiazem, felodipine, isradipine, nicardipine, nifedipine, nisoldipine and verapamil; other anti-hypertensive agents such as clonidine, diazoxide, fenoldopan, hydralazine, minoxidil, nitroprusside, phenoxybenzamine, epoprostenol, tolazoline, treprostinil and nitrate-based agents; anti-coagulant agents, including heparins and heparinoids such as heparin, dalteparin, enoxaparin, tinzaparin and fondaparinux; other anti-coagulant agents such as hirudin, aprotinin, argatroban, bivalirudin, desirudin, lepirudin, warfarin and ximelagatran; and/or anti-platelet agents such as abciximab, clopidogrel, dipyridamole, optifibatide, ticlopidine and tirofiban.

Other therapeutic agents may include, but are not limited to, prostaglandin PDE-5 inhibitors and other prostaglandin agents such as alprostadil, carboprost, sildenafil, tadalafil and vardenafil; thrombin inhibitors; antithrombogenic agents; anti-platelet aggregating agents; thrombolytic agents and/or fibrinolytic agents such as alteplase, anistreplase, reteplase, streptokinase, tenecteplase and urokinase; anti-proliferative agents such as sirolimus, tacrolimus, everolimus, zotarolimus, paclitaxel and mycophenolic acid; hormonal-related agents including levothyroxine, fluoxymestrone, methyltestosterone, nandrolone, oxandrolone, testosterone, estradiol, estrone, estropipate, clomiphene, gonadotropins, hydroxyprogesterone, levonorgestrel, medroxyprogesterone, megestrol, mifepristone, norethindrone, oxytocin, progesterone, raloxifene and tamoxifen; anti-neoplastic agents, including alkylating agents such as carmustine lomustine, melphalan, cisplatin, fluorouracil3, and procarbazine antibiotic-like agents such as bleomycin, daunorubicin, doxorubicin, idarubicin, mitomycin and plicamycin; anti proliferative agents (such as 1,3-cis retinoic acid, 5-fluorouracil, taxol, rapamycin, mitomycin C and cisplatin); antimetabolite agents such as cytarabine, fludarabine, hydroxyurea, mercaptopurine and 5-flurouracil (5-FU); immune modulating agents such as aldesleukin, imatinib, rituximab and tositumomab; mitotic inhibitors docetaxel, etoposide, vinblastine and vincristine; radioactive agents such as strontium-89; and/or other anti-neoplastic agents such as irinotecan, topotecan and mitotane.

Administration of RPCs and Methods of Treatment

Also provided herein are methods and uses of cultured retinal progenitor cells prepared as a cell suspension and used as allogeneic grafts for treatment of patients with retinal disease. For example, provided herein are cell-based therapies comprising or consisting of use of cultured heterogeneous cell populations from an immature mammalian, e.g., human retina.

Cell populations and related compositions described herein may be provided to a subject or patient by a variety of different means. By way of non-limiting example, they can be provided locally, e.g., to a site of actual or potential injury or disease. In one embodiment, they are provided using a syringe or needle to inject the compositions at a site of possible or actual injury or disease. In other embodiments, they are provided systemically, e.g., administered to the bloodstream intravenously or intra-arterially. The particular route of administration will depend, in large part, upon the location and nature of the disease or injury being treated or prevented.

Accordingly, the methods described herein include providing a cell population or composition via any known and available method or route, including but not limited to intraocular, oral, parenteral, intravenous, intra-arterial, intranasal, and intramuscular administration.

The determination of suitable dosages and treatment regimens may be readily accomplished based upon information generally known in the art and obtained by a physician.

By way of non-limiting example, the cell dose may be between about 0.3 and about 0.5 million cells (e.g., 0.3, 0.31, 0.32, 0.33, 0.34, 0.35, 0.36, 0.37, 0.38, 0.39, 0.4, 0.41, 0.42, 0.43, 0.44, 0.45, 0.46, 0.47, 0.48, 0.49, or 0.5 million cells) or between 0.5-3 million cells (e.g., 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, or 3 million cells).

The efficacy results observed between both dose ranges are roughly similar. However, there is a possible increased risk with larger doses (e.g., 2-9 million cells) of the cells persisting in the visual axis, sticking to posterior lens capsule, and/or entering anterior chamber (pseudo-hypopyon) if the patient's eye has weakened zonules. Moreover, those skilled in the art will recognize that it is possible that the duration of graft survival might be proportional to dose and, thus, the original graft size.

Dosing frequency of allogeneic hRPCs in the vitreous cavity will be important. In various embodiments, subsequent doses (i.e., "redoses") can be made to the same eye of the patient or to the fellow eye. Redosing the fellow eye in both animal models as well as a number of patients has been performed without subsequent immune sequelae, thereby suggesting the redosing will be well-tolerated bilaterally (and, presumably, in the same eye, as has been performed in animals up to 3 times).

Grafts can survive in patients with RP for a year or more. However, as they tend to disappear from the vitreous after approximately 1-1.5 years, this suggests that redosing within approximately a 1-2 year time frame might not be too aggressive and, in fact, may become the future norm in a majority of cases.

In any of the methods disclosed herein, treatment may involve a single treatment or multiple (e.g., 2, 3, 4, 5, 6, or more) treatments. In particular, for preventative purposes, it is contemplated in certain embodiments that purified cell populations are administered following a stress that might potentially cause retinal injury.

In one embodiment, the cell populations and compositions may be locally administered as a single injection to the vitreous cavity or subretinal space of the subject.

While the compositions and methods described herein are not limited by any particular mechanism of action, an exemplary mechanism of action is diffusible and/or trophic. Evidence is consistent with concept of trophic reprogramming of moribund host cones, resulting in switch from apoptotic trajectory to regeneration of photic processing capability. This can be direct or indirect. Involvement of other ocular tissues not ruled out. This mechanism allows for placement of a graft of a heterogeneous mixture of fetal neural retinal cells in a vitreous or a subretinal space.

Vitreal placement enhances diffusion-based treatment effect. This mechanism can allow a graft of heterogeneous mixtures of fetal neural retinal cells to be placed out of the visual axis, yet still treat patient's macula. Moreover, a vitreal placement is used to greatly simplify a treatment, as this exemplary treatment can increase availability to needy patients worldwide. Additionally, vitreal placement may aid in immune tolerance by being remote to vasculature. Those skilled in the art will recognize that vitreal placement avoids potential complications of subretinal surgery, avoids risks of general anesthesia, does not require that a hole (retinotomy) be made in retina (which raises risk of retinal detachment, bleeding), and/or does not require the patient's retina undergo a focal detachment (focal detachment can lead to photoreceptor damage or loss, retinal tears, bleeding, global retinal detachment and, in RP, detachment of the thin, atrophic, and adherent retina will be a difficult/risky procedure).

In some embodiments, the cells are placed in the vitreous cavity using a suitable needle size and length. Ideally, the syringe has a minimal (e.g., 1 microliter) dead space, in order to enhance the efficiency of delivery and avoid loss of product due to retention in the syringe. The use of a short needle (e.g., 31 G (gauge) with 5/16 inch length or 30 G with a ½ inch length) allows for maximum convenience (i.e., suitability for use in a clinical or office setting). However, the use of a longer needle length (e.g., 27 G or 25 G with a ⅝ inch length) allows for optimum placement (used under operating scope) further back (posterior) in the vitreous, closer to the macula. Determination of the appropriate needle size and length is within the routine level of skill in the art. When choosing the appropriate needle size and length, it is important that cell viability remain above the requisite threshold value after cells were passed through needle.

Placement of the cells within the anterior vitreous is simple and allows for maximum safety and convenience. In contrast, placement in the posterior vitreous (near the posterior pole) requires direct visualization of needle tip to avoid penetrating injury of retina. However, this may enhance the overall treatment effect and may represent the optimal placement and efficacy.

While retinal cell replacement is possible, it is not required for clinical efficacy. Likewise, donor cell migration into retina is possible but is not required for clinical efficacy; donor cell integration in retinal circuitry is possible but is not required for efficacy; donor cell integration into the outer nuclear layer/macula of host retina is possible but is not required for efficacy; and/or donor cell integration into retina is possible but is not required for sustained graft survival.

In some embodiments, the RPC cells can be injected in a vitreous cavity where, optionally, no vitrectomy or subretinal surgery is required. However, some embodiments may involve the optional use of one or more of vitrectomy, core vitrectomy, and/or a vitreolytic agent to remove vitreous gel and optimize mobility and penetration of injected cells to the posterior vitreous (e.g., the optimal location in proximity to posterior pole of eye). In some cases, use of surgical vitrectomy may enhance placement of cells in the eye.

The cells can also be implanted into (e.g., injected into) a subretinal space, or, they can be implanted into (e.g., injected into) an eye using any standard intraocular injection procedure, e.g., using a hypodermic or an angled insertion pathway. In some embodiments, no retinotomy or no intraocular gas or silicon oil is required.

Alternatively, an anterior chamber paracentesis can optionally be performed, depending on situation, as determined by one of skill in the art. In some embodiments, no suturing of globe is needed during and/or after a procedure.

Any of the methods disclosed herein may include the step of administering the compositions under topical anesthesia directly to the vitreous cavity, without need for systemic immune suppression of the subject. Additionally, while tissue typing of graft and matching to patient or subject is not required, it may be performed if desired, for example using any tissue typing and matching techniques known to those skilled in the art.

As noted, in any of the methods described herein, only topical anesthesia can be used, e.g., no local, regional, general anesthesia used. However, in some cases, local, regional or general anesthesia may additionally or alternatively be used during administration. Examples of suitable local anesthetics suitable for use in the methods disclosed herein include, without limitation, mepricaine, proparacaine, prilocaine, ropivacaine, benzocaine, bupivacaine, butamben picrate, chlorprocaine, cocaine, dibucaine, dimethisoquin, dyclonine, etidocaine, hexylcaine, ketamine, lidocaine, mepivacaine, pramoxine, procaine, tetracaine, salicylates and derivatives, esters, salts and mixtures thereof.

In certain embodiments, no anti-inflammatory and/or immune suppression (i.e., systemic immune suppression) is required. Moreover, clinical experience supports that none is needed, as, in some cases, graft survival can be seen over many months, for example, including and exceeding 1 year.

However, if necessary, anti-inflammatory and/or immune suppression therapy as post-operative drops can be included. For example, patients may be treated post-injection with topical steroid eye drops, with administration tapering over 1 week, or, alternatively, after up to 2 weeks, if indicated clinically for evidence of persistent post-treatment inflammation.

In alternative embodiments, there is no mandatory bed rest, post-op and/or need for "face-down" positioning. These methods can be performed an outpatient procedure and, likely do not require any overnight hospital stay.

In some embodiments, during administration, the patient's head is tilted back from reclined seated position, as close to horizontal as possible, in order to maximize settling of injected cells within the vitreous gel towards the posterior pole of eye, which is the most important part of retina for vision. Patients should maintain this position for approximately 30 minutes or more, as tolerated by patient. In addition, following administration, patients should also spend time laying on back, looking up, at home.

Any of the compositions and methods described herein involving or using heterogeneous mixtures of fetal neural retinal cells (e.g., retinal progenitor cells) for treating, ameliorating or preventing a retinal disease or condition, e.g., Usher's disease, retinitis pigmentosa (RP), a degenerative retinal disease, an age related macular degeneration (AMD), a wet AMD or a dry AMD, geographic atrophy, a retinal photoreceptor disease, a diabetic retinopathy, cystoid macular edema, uveitis, a retinal detachment, a retinal injury, macular holes, macular telangiectasia, a traumatic or an iatrogenic retinal injury, a ganglion cell or optic nerve cell disease, a glaucoma or an optic neuropathy, an ischemic retinal disease such as retinopathy of prematurity, retinal vascular occlusion, or ischemic optic neuropathy; or improving a photopic (day light) vision; or for improving correcting visual acuity, or improving macular function, or improving a visual field, or improving scotopic (night) vision.

Likewise, any of the compositions or methods described herein can be used to provide a rapid effect, increased best-corrected visual acuity, improved macular function, and/or the possibility of preserving or regaining central fixation.

Using or practicing any of the compositions and methods disclosed herein results in various systemic benefits, e.g., changes in appearance in treated individuals possibly due to somatic improvements, which could be related to effect of light on circadian rhythms, pituitary function, release of hormones, vascular tone, etc.; improved sense of visual capabilities; improved ambulatory independence; improved sense of well-being; and/or improved activities of daily living.

In alternative embodiments, using or practicing any of the compositions and methods disclosed herein does not result in development of unwanted cell growth, e.g., tumors; infections, e.g., no endopthalmitis—a risk for any intraocular procedure; transmission of disease (however, prion or mad cow disease may be difficult to rule out); uveitis and/or acute graft rejection; elevated intraocular pressure; angle closure; hypotony; retinal detachment; and/or neovascularization.

The uses and methods described herein can rapidly and sustainably restore and/or preserve clinically significant degrees of visual function in a retina in mammalian subjects, including but not limited to, improved photopic (day light) vision, increased best-corrected visual acuity, improved macular function, preserving or regaining central fixation, improved visual field, improvements in scotopic (night) vision, increased or improved sensitivity to sound, and improvements in visual acuity in a contralateral eye. Other changes may include various systemic benefits, e.g., changes in appearance due to somatic improvements, which could be related to effect of light on circadian rhythms, pituitary function, release of hormones, vascular tone; an improved sense of visual capabilities; improved ambulatory independence; improved sense of well-being; and/or improved activities of daily living. Such changes in vision can be measured by methods known in the art.

Visual benefits may be rapid and may occur within first week post-treatment, but may also occur as incremental benefits over longer periods of time. Retinal cell replacement and/or donor cell migration into the retina, retinal circuitry, or outer nuclear layer or macula may occur, but is not required for clinical efficacy; donor cell migration into retina is possible, but not required for clinical efficacy.

Measuring changes in vision, including improvements in vision resulting from treatment with the retinal progenitor cell compositions disclosed herein can be achieved using standard ophthalmic examination techniques, including but not limited to, fundus examination, best corrected visual acuity (BCVA), TOP, slit lamp examination, fluorescein angiography (FA), Optical Coherence Tomography (OCT), stereo-fundus photography, electroretinography (ERG), cone flicker electroretinography, perimetry (visual field), microperimetry, dark adaptation, maze negotiating skill, optokinetic/optomotor responses, pupillary responses, visual evoked potentials (VIP), and adaptive optics scanning laser ophthalmoscopy (AOSLO).

In vivo animal data has also suggested that intravitreal RPCs are a means of influencing multiple cell types in the diseased retina, including, but not limited to, Mueller cells (enhanced activation in retinal degeneration and/or increased local expression of glutamine synthetase (GS)); vascular compartment in diabetic retinopathy (less vascular permeability (leakage) and/or less ischemia based on decreased intra-retinal VEGF levels); enhanced recruitment of macrophages in retinal degeneration; increased local expression of bFGF (neurotrophic factor) in retinal degeneration; decreases expression of caspase 3 is decreased (indicating less retinal cell death). Thus, administration of RPCs could also be useful in a range of other retinal diseases, disorders, and conditions.

In addition, preliminary evidence of a crossover treatment effect in terms of indications of efficacy in the un-injected fellow eye has been observed. Specifically, this was seen in RCS rats (histological rescue of photoreceptors as well as ERG recordings) and also in a subset of patients (visual acuity testing), and it appears to be evidence of a "humoral" treatment effect that can extend beyond the confines of the injected eye. It is possible that this effect might be the result of the diffusion of cytokines and/or exosomes through the blood circulation, immune modulation, or both.

Likewise, in vivo data in animals suggests that a single intravitreal injection of osteopontin protein (OPN) alone replicates some, but not all, of the treatment effect provided by hRPCs. However, the effects of a single dose of pleiotrophin (PTN) and/or midkine differed from those observed with OPN in terms of timing and specific responses of the retinal cell populations.

In vivo data in animals also suggests that a single intravitreal injection of RPC-derived exosomes replicates, to some extent, the treatment effect provided by hRPCs.

Kits and Instructions

Also provided are kits containing any of the compositions described herein (e.g., a heterogeneous mixture of fetal neural retinal cells) suitable for use in any of the methods disclosed herein (e.g., treating a retinal disease or condition, or making or isolating a heterogeneous mixture of fetal neural retinal cell), including instructions for use thereof. Also provided are kits containing a composition, product of manufacture, or mixture or culture of cells (e.g., heterogeneous mixture of fetal neural retinal cells), wherein optionally the kit further includes instructions for practicing any of the methods described herein.

Kits may also include a cell population containing the mammalian retinal progenitor cells described herein, whether provided as cells in culture, fresh or frozen, or formulated as a composition for administration into a subject. Likewise, the kit may further include instructions for practicing any of the methods described herein. In some embodiments, such kits may additional contain an agent that binds one or more marker of retinal progenitor cells described herein (e.g., an antibody or oligonucleotide primer) and/or a basal or conditioned medium. For example, suitable kit may include: a first container containing an antibody specific for one or more markers, wherein said antibody is adapted for isolation or detection, e.g., by being conjugated to a fluorescent marker or magnetic bead; and a second container containing basal or conditioned medium. The kits may further include one or more additional reagents useful in the preparation of a cell population as provided herein, such as cell culture medium, extracellular matrix-coated cell culture dishes, and/or enzymes suitable for tissue processing. The kit may also include instructions regarding its use to isolate, purify, and/or expand the retinal progenitor cells or cell populations obtained from a tissue sample. Likewise, the kits may further contain a means for obtaining a tissue sample from a patient or donor, and/or a container to hold the tissue sample obtained.

Veterinary Applications

Any of the compositions and methods described herein can also be used for veterinary applications. For example, growing of feline RPCs, and the therapeutic application to the retina in a dystrophic cats and other animals, e.g. any mammalian pet, common domesticated and rare wild mammalian species, zoo animals, farm animals, sport (e.g., racing dogs or horses) animals, and the like.

There are a number of domesticated animals that harbor genes causing blindness as a result of extensive inbreeding. These included cats, dogs, and horses, and probably other species.

Likewise, there are retinal diseases and injuries that occur in wild and domestic animals that will benefit from treatment using the compositions and methods described herein.

Products of Manufacture, Implants and Artificial Organs

Also provided are implants and artificial organs, bioreactor systems, cell culture systems, plates, dishes, tubes, bottles and flasks and the like including one more of the compositions described herein containing a heterogeneous mixture of fetal neural retinal cells.

By way of non-limiting example, additionally provided herein are a bioreactor, implant, stent, artificial organ or similar devices containing a heterogeneous mixture of fetal neural retinal cells; for example, implants analogous to or as described in U.S. Pat. Nos. 7,388,042; 7,381,418; 7,379,765; 7,361,332; 7,351,423; 6,886,568; 5,270,192; and U.S. Pat. App. Pub. Nos. 20040127987; 20080119909 (describing auricular implants); 20080118549 (describing ocular implants); 20080020015 (describing a bioactive wound dressing); 20070254005 (describing heart valve bio-prostheses, vascular grafts, meniscus implants); 20070059335; 20060128015 (describing liver implants).

ENUMERATED EMBODIMENTS

The invention may be defined by reference to the following enumerated, illustrative embodiments:

1. A method of isolating primary retinal cells obtained from a human sample by:
   a) processing an obtained sample of human retinal tissues from a human donor of about 12 weeks to about 28 weeks gestational age,
   b) mechanically dissociating the obtained sample,
   c) determining the viability and quantity of the primary retinal cells obtained from the sample, and
   d) confirming the morphology of the obtained primary retinal cells to generate a dissociated suspension of cells and cell clusters.
2. The method of embodiment 1, wherein the human retinal tissue is obtained from one or a pair of human eyeballs.
3. The method of embodiment 2, wherein the eyeball(s) possess a normal morphology comprising intact globes, clear cornea, normal shape, or any combination thereof.
4. The method of embodiment 1, wherein the human retinal tissue is stored in RPMI-1640 medium with L-glutamine and stored on ice immediately after tissue harvest from the human donor.
5. The method of any one of embodiments 1-4, wherein the stored human retinal tissue is delivered and used within a defined period of time following harvest.
6. The method of embodiment 5, wherein the define period of time comprises between about 7 to about 26 hours.
7. The method of embodiment 1, wherein step (a) comprises:
   a) following tissue harvest, removing the eyeball(s) from the RPMI-1640 medium and rinsing 1 to 5 times with ice cold phosphate buffered saline (PBS) supplemented with antibiotics,
   b) removing an optic nerve and mesenchymal tissue from the eyeball to remove all extra-ocular cells,
   c) washing the eyeball with ice cold PBS supplemented with antibiotics,
   d) puncturing the globe at the limbus using a needle,
   e) circumferentially cutting along the limbus with microsurgical scissors,
   f) removing a lens, cornea, and associated vitreous body,
   g) dissociating the retina(s) from the retinal pigment epithelium (RPE) layer to produce isolated retinas,
   h) placing the isolated retina(s) in a Petri-dish containing ice cold medium or PBS supplemented with antibiotic.
8. The method of embodiment 1, wherein step (b) comprises mechanically dissociating the retina(s) obtained in step (a) by:
   a) transferring the retina(s) to a conical tube,
   b) mechanically dissociating the retina(s) to produce dissociated retinas,
   c) washing the Petri-dish with a serum-free medium supplemented with an antibiotic and transferring medium containing any residual dissociated retinas to the conical tube containing the dissociated retina(s),
   d) pelleting the dissociated retina(s) via centrifugation, and
   e) removing the supernatant.
9. The method of embodiment 8, wherein the mechanical dissociation of the retina is performed via trituration with a sterile pipet.
10. The method of embodiment 8, wherein the dissociated retina is pelleted via centrifugation at 10 to 1000 g for period between 0 and 30 minutes at 1 to 50° C.
11. The method of embodiment 1, wherein step (c) comprises:
   a) resuspending the pelleted retinal tissue from step (b) in ice cold antibiotic-supplemented serum-free medium,
   b) determining the quantity and viability of retinal cells and retinal cell clusters obtained from the mechanical dissociation of the retinal tissue, c) seeding the cells into fibronectin-coated cell culture flasks containing antibiotic-supplemented serum-free medium,
d) incubating the retinal cell containing flasks at 10 to 50° C.

12. The method of embodiment 11, wherein the quantity and viability of cells are measured by an NC-200 cell counter.

13. The method of embodiment 11, wherein the counted number of cells is between about 1 and about 1,000,000,000.

14. The method of embodiment 11, wherein the percentage of viable counted cells is between about 10 and about 100.

15. The method of embodiment 11, wherein the flasks are seeded with between about 1 and about 1,000,000,000 cells.

16. The method of embodiment 11, wherein the incubation of retinal cell containing flasks is at 37° C. under 0 to 30% $CO_2$ and 0 to 50% $O_2$.

17. The method of embodiment 1, wherein step (d) comprises confirming that retinal cells seeded into cell culture flasks consist of retinal cell clusters that contain about 1 to about 100 cells.

18. The method of any one of embodiments 1-17, wherein the antibiotic used to supplement PBS or serum-free medium is gentamycin.

19. The method of any one of embodiments 1-18, wherein the antibiotic is used at a concentration of about 0 to about 10,000 µg/mL.

20. The method of any one of embodiments 1-19, wherein serum-free medium comprises:
a) Advanced DMEM/F12,
b) N-2 supplement,
c) EGF (recombinant human epidermal growth factor),
d) bFGF (basic fibroblast growth factor), and
e) GlutaMAX I.

21. A method of culturing isolated primary human retinal cells to produce a population of non-immortal human retinal progenitor cells comprising:
a) culturing a suspension of isolated primary retinal cells in serum-free media in culture flasks or plates coated with a xeno-free fibronectin, an ornithine, a polylysine, or a laminin at standard oxygen levels for between about 4 and 6 passages,
b) subsequently culturing the suspension in serum-free media at low oxygen levels for between about an additional 3 and 6 passages, wherein the cells are passaged at between 40% to 90% confluence and treated with an enzyme at each passage to dissociate the cells and adding fresh culture media, and
c) subsequently cryopreserving the cells, thereby making a population of non-immortal human retinal progenitor cells.

22. The method of embodiment 21, wherein, following the subsequent culturing of the suspension at low oxygen levels, the cells are allowed to grow without passaging for a period of time at standard oxygen levels.

23. The method of embodiment 21, wherein the period of time between passages is 3 to 5 days.

24. The method of embodiment 21, wherein the enzymatic solution used to dissociate cells comprises trypsin or equivalent.

25. The method of embodiment 21, wherein the cells are dissociated at passage 1 using an enzymatic solution comprising trypsin or equivalent, and EDTA at a 1:4 ratio for between 6-10 minutes at 37° C.

26. The method of embodiment 21, wherein the cells are dissociated at passage 2 using an enzymatic solution comprising trypsin or equivalent, and DPBS at a 1:1:3 ratio for between 4 to 8 minutes at 37° C.

27. The method of embodiment 21, wherein the cells are dissociated at passage 3 and all further passages using an enzymatic solution comprising trypsin or equivalent, EDTA, and DPBS at a 1:1 ratio for between 4 to 8 minutes at 37° C.

28. The method of embodiment 21, wherein the dissociation is halted by addition an excess of DMEM or PBS.

29. The method of embodiment 21, wherein cell count and viability is determined following dissociation.

30. The method of embodiment 21, wherein the cell count and viability are determined via NC-200 cell counter.

31. The method of embodiment 21, wherein the cryopreservation of step (c) is performed by:
a) enzymatically dissociating the cells using 1:1 trypsin or equivalent, and DPBS,
b) halting the dissociation with an excess of DMEM or PBS,
c) pelleting the cells via centrifugation at between 10 and 10,000 g for 1 to 30 minutes,
d) resuspending the cells in serum-free medium and determining the total cell count and viability,
e) adding cryopreservation medium to achieve a final DMSO concentration of between 5 and 30%,
f) aliquoting 0.2 to $100 \times 10^6$ cells into each cryovial,
g) freezing each vial at −80° C. for 6 to 72 hours, and
h) placing each vial of cells in liquid $N_2$.

32. The method of embodiment 21, wherein the cells and/or cell clusters are cultured together with supplements or additives that support cell survival or growth.

33. The method of embodiment 32, wherein the supplements or additives that support cell survival or growth are selected from the group consisting of L-glutamine, human recombinant growth factors consisting of EGF and bFGF (Invitrogen), and other growth factors.

EXAMPLES

Example 1: Isolation of Primary Retinal Cells: Protocol A

Isolation of primary human retinal cells were prepared following a protocol specifically optimized for a 4.5 to 21.5 hour transportation interval where the transportation interval is measured from the time of tissue harvest to the time the donor tissue is received.

1. From a 17 to 18 week gestational age fetus, 1 or pair of eyeballs in 15 ml tube with RPMI-1640 medium with L glutamine (BioWhittaker) is shipped on ice and delivered within 4.5 to 21.5 hrs. Upon receipt, inspect the eyeball(s) for gross abnormalities: globe intact, cornea is clear, eyeball has normal shape. Steps 2-8 are performed in a laminar flow hood using sterile technique 2. Rinse whole eyeballs by 40 ml cold PBS containing antibiotics (in 50 ml tube) for 3 times (in 3 different tube).

3. The optic nerve and remaining mesenchymal tissue were removed. This approach is taken to avoid possible contamination of retinal isolates with brain-derived cells. Rinse by cold PBS containing antibiotics one more time.

4. Under dissection microscope, puncture the whole at the limbus using a 1 ml syringe with 25$^{5/8}$ needle, open the eyeball circumferentially by cutting along the limbus using microsurgical scissors, remove the cornea, lens and associated vitreous body. The retina is carefully teased away from the RPE, harvest into small Petri-dish containing ~2 ml cold DMEM/F12.

5. Break retina into small pieces using a 1 mL tip in the Petri-dish manfully (2 to 5 times), transfer into 15 mL cold conical bottom tube, rinse petri-dish 2 to 3 times by 1 mL cold PBS, add into 15 mL tube, spin down, 1000 rpm (179×g) for 5 minutes, completely remove supernatant by 10 mL pipet and polished glass pipet.

6. Add 0.8 mL undiluted TrypLE Express (Invitrogen) for 40 sec at room temperature, gently and slowly pipette using a 1 mL tip (about 10 times), add 10 mL cold fresh medium (no serum) to neutralized TrypLE Express, spin down, 1000 rpm (179 g)×4 min, remove the supernatant, re-suspend the pellet using 1.5 ml cold fresh medium (SM), pipet using polished glass pipet about 10 times, add additional 6.5 mL of medium, cell viability and cell number are determined by Trypan Blue (Invitrogen) staining, counted by Countess (Invitrogen) or manually, about $1.3×10^6$ cell/ml, about 92% alive, about $10×10^6$ cell clusters/total, about 80% are small/medium clusters. Seed cells into 2 T75 coated by fibronectin (See example 5), followed by incubation at 37° C. under 5% $CO_2$, 3% or 20% $O_2$ (optionally 37° C., 5%-10% $CO_2$, 1%-20% $O_2$ incubation).

Note: defined cell counting.
Single cells: ~6-8 um, containing 1 cell.
Small cluster: ~15-40 um, containing ~2-30 cells.
Medium cluster: ~40-100 um, containing ~30-80 cells.
Large cluster: ~100-150 um, containing >80 cells.
In the resulting cell population: ~80-90% are small or medium clusters, ~9-18% single cells, ~1-2% large clusters.
If small/medium clusters are counted as "one", total cell number is $~10×10^6$.
If the single cells are counted as "one", total cell number is $~240×10^6$.

7. Total procedure: 45 min~1 hr 10 min. (Optionally within 2 hours).

8. ~1.5 hour later, 90% cells have settled down the bottom (if the tissue is fresh such as 4.5 hours shipping on ice, if not, such as 21.5 hours shipping on ice, ~6 hours settle down the bottom), 90% are small chunks, 10% are single cells. In general 90% are live (good), cell density will be >10% confluence (~20% is better) as assessed by IncuCyte. Take photograph.

Example 2: Isolation of Primary Retinal Cells: Protocol B

Isolation of primary human retinal cells was performed following a protocol specifically optimized for a 7 to 26 hour transportation interval where the transportation interval is measured from the time of tissue harvest to the time the donor tissue is received.

1. From a 17 to 20 week gestational age fetal tissue donation, 1 or a pair of eyeballs in a 15 ml tube containing RPMI-1640 medium with L glutamine (Bio-Whittaker), is shipped on ice and delivered within a 7-26 hour transportation window. The protocol can also work for a broader transport window. Upon receipt, inspect eyeball(s) for gross abnormalities: globe intact, cornea clear, eyeball should have normal shape. Gentamicin at 50 μg/mL is added to the RPMI-1640 and L glutamine transport medium to prevent potential tissue contamination.

Steps 2-8 are performed in a laminar flow biosafety cabinet using sterile technique 2. Rinse intact eyeballs in 40 ml cold PBS containing antibiotics (in 50 ml tube) 3 times (in 3 different tubes). Gentamicin at 30 μg/mL is used. Gentamicin is used instead of Penicillin or Streptomycin to avoid excluding patients with antibiotic allergies.

3. The optic nerve and remaining mesenchymal tissue are removed from eye(s) to avoid possible contamination of retinal isolates with extra-ocular cells. Rinse with cold PBS containing antibiotics one additional time.

4. Under a dissecting microscope, puncture the globe at the limbus using a 1 ml syringe with 25$^{5/8}$ needle, open the eyeball circumferentially by cutting along the limbus using microsurgical scissors, remove and discard the cornea, lens and associated vitreous body. The retina can be carefully teased away from the underlying RPE layer, transferred to a small Petri-dish containing about 2 mL cold, Complete medium with Gentamicin (Gentamicin 30 μg/ml).

5. Transfer retina into a 15 mL conical tube. Break retina into small pieces using gentle trituration via a 1 ml pipette tip (4 to 8 times). If residual retinal tissue is present in Petri dish rinse the dish 1 to 2 times using 1 mL cold complete medium with Gentamicin, and add to the 15 ml tube containing the retinal tissue. Transfer 15 mL tube to centrifuge, spin down at 140×g for 3 minutes at 4° C., aspirate and completely remove supernatant.

6. Re-suspend the pellet in 1.0 mL cold fresh medium with Gentamicin using 1 mL tip, pipet, gently pipetting the suspension 4 to 5 times, add additional 15 mL medium. Cell viability and cell number are determined via NC-200 using the aggregate cell counting method. This method can get an accurate cell number while maintaining cell clusters, which can be important for initial cell culture, and transforming a tissue into cells. Cell viability is anticipated to fall into the range of 68-85%, live cells counts are anticipated to be about $73-147×10^6$. Seed cells into 3×T25 (or 1-2 T75) flasks previously coated with fibronectin (See Example 5), followed by incubation at 37° C. under 5% $CO_2$, 20% $O_2$. (Note: 20% is for step 1: tissue to seed bank, which can also be done under low oxygen condition. However the goal here was to keep the new product as close as possible to previous products, which were grown under 20% oxygen. Step 2: seed bank to production bank, is done using low oxygen 3% culture, to prolong the cell proliferation.)

7. Check cells under microscope: cultures are expected to predominantly consist of small-to-medium sized clusters, plus some single cells (the latter more likely to be non-viable).

8. Duration of total isolation procedure: about 30 to 60 minutes (this protocol specifically omitting enzymes is significantly faster to perform and simpler than an enzyme-based isolation protocol).

Example 3: Cell Culture: Protocol A

Human retinal progenitor cells were cultured from the retinal cells isolated from the method described in Example 1:
1. Change medium: 90% change medium every 2 days.
2. Passage: cells are passaged at 60-80%, optionally 40-90% confluence, by TrypLE Express (Invitrogen), optionally trypsin or equivalent, or TRYP-LE EXPRESS or equivalent, 2 times dilute (equivalent 0.125%), 5-6 min, 37° C. incubation. Dissociation is stopped by adding old medium or cold PBS 10 ml. cell viability and cell number are determined by Trypan Blue (Invitrogen) staining, counted by Countess (Invitrogen) or manually, cell viability >90%. Seed the cells into new fibronectin coated flask/plate at density 1-6.7× $10^4$/cm$^2$ (early passage 6.7×$10^4$ clusters/cm$^2$), late passage: 2×$10^4$/cm$^2$).
3. Freeze cells: cells are harvested by TrypLE Express (Invitrogen), optionally trypsin or equivalent, or TRYP-LE EXPRESS or equivalent, 2 times dilute (equivalent 0.125%), 5-6 min, 37° C. incubation. Dissociation is stopped by adding old medium or cold PBS 10 ml. spin down, 1000 rpm (179×g) for 5 minutes, re-suspend cells in fresh medium or cold PBS. Cell viability and cell number are determined by Trypan Blue (Invitrogen) staining, counted by Countess (Invitrogen) or manually. Spin down, 1000 rpm (179×g) for 5 minutes, re-suspend cells in cell freeze medium, aliquot 0.5-5×$10^6$ cells in each cryovial (Greiner). Put into Cryo 1° C. freezing container (NALGENE), place to −80° C. freezer overnight (or longer, <2 weeks), transfer to liquid nitrogen tank.
4. Thaw cells: cells are taken out from liquid nitrogen, left in 37 C water bath for 2-3 min until crystals disappear, transferred into one cold 15 ml conical bottom tube immediately by 1 ml tip, rinse vial by cold fresh medium 2 times, slowly add 12 ml cold fresh medium into 15 ml tube, the first 1 ml drop by drop, gently shaking. Spin down at 800 rpm (115 g) for 3 minutes. Discard the supernatant, re-suspend the cell pellet in fresh medium, determined the cell number and viability, describe above. Seed into new coated flask incubate at the condition describes above.
5. Prepare cells for transplantation: cells are harvested by TrypLE Express (Invitrogen), optionally trypsin or equivalent, or TRYP-LE EXPRESS or equivalent, 2 times dilute (equivalent 0.125%), 5-6 min, 37° C. incubation. Dissociation is stopped by adding old medium or cold PBS 10 ml. Spin down, 1000 rpm (179×g) for 5 minutes, re-suspend cells in 10 ml cold HBSS, cell viability and cell number are determined by Trypan Blue (Invitrogen) staining, counted by Countess (Invitrogen) or manually. Spin down, 1000 rpm (179×g) for 5 minutes, re-suspend cells in cold HBSS, making cell suspension for transplantation, 0.5×$10^6$ cells in 100 ul HBSS for patient, 30,000 cells in 2 ul HBSS for rat.

Example 4: Cell Culture: Protocol B

Human retinal progenitor cells were cultured from the retinal cells isolated from the method described in Example 2:
1. Change medium: 100% medium change, change every 2 days, except day0-day3. Open systems, closed systems, and semi-closed systems can all work for changing media and passaging cells. Optionally, medium can be changed daily.
2. Passaging: cells are passaged every 4-5 days at 15-95% confluence, optionally 40-95% confluence. Method differs by passage number. Cells can also be passaged every 3-4 days, or every 3-5 days.

Passage 1: TrypLE Select (Invitrogen)+EDTA (Invitrogen) at 1:4, for 7-8 min at 37° C. incubation.

Passage 2: TrypLE Select (Invitrogen)+EDTA (Invitrogen)+DPBS (Invitrogen) at 1:1:3, for 5-6 min at 37° C. incubation. T Passage 3, and later: TrypLE select (Invitrogen)+DPBS at 1:1, 5-7 min at 37° C. incubation.

Optionally TrypLE Express, trypsin or equivalent, or TRYP-LE EXPRESS or equivalent, 2 fold dilution (equivalent 0.125%) can be used. Dissociation of clusters is stopped by adding DMEM or PBS (10 ml). Cell viability and cell number are determined via NC-200. Expected cell viability >70%. Seed the cells into new fibronectin coated flask/plate at density 3-67×$10^4$/cm$^2$ (early passage 67×$10^4$/cm$^2$, later passage: 3×$10^4$/cm$^2$).
3. Cryopreservation: cells are harvested using TrypLE Select/Express (Invitrogen), optionally trypsin or equivalent, or TRYP-LE EXPRESS or equivalent, at 2 fold dilution (equivalent 0.125%), for 5-7 min, 37° C. incubation. Dissociation stopped by adding DMEM or PBS. Then spin down. For 50 ml tube: 490×g for 7 minutes, for 500 ml conical bottle, 700×g for 8 minutes, re suspend cells in fresh medium. Cell viability and cell number are determined using NC200. Add same amount of 2× cryopreservation medium (20% DMSO) to achieve final 10% DMSO for cell suspension. Aliquot 0.5-10×$10^6$ cells into each cryovial (Themofisher or similar). Put into Cryo 1° C. freezing container (NALGENE), place in −80° C. freezer overnight (or longer, <2 weeks), transfer to liquid nitrogen tank.
4. Thaw cells: cells are taken out of liquid nitrogen, left in 37° C. water bath for 2-3 min until crystals disappear, then transferred into one cold 15 ml conical bottom tube immediately using 1 ml tip, rinse vial with cold fresh medium 1-2 times, slowly add 9-12 ml cold fresh medium into 15 ml tube, spin down at 1200 rpm (300 g) for 5 min. Discard the supernatant, re-suspend the cell pellet in fresh medium, determined the cell number and viability, as described above. Seed into new coated flask and incubate under the conditions described above.
5. Prepare cells for transplantation: cells are harvested by TrypLE Express (Invitrogen), optionally trypsin or equivalent, or TRYP-LE EXPRESS or equivalent, 2 fold dilution (equivalent 0.125%), 5-6 min, 37° C. incubation. Dissociation is stopped by adding DMEM. Cell suspension is spun down, 300 g×5 min, then re-suspend cells in 0.5-3 ml cold BSS Plus (or BSS/DPBS/HBSS). Cell viability and cell number are determined using Trypan Blue (Invitrogen), counting via Countess (Invitrogen) or manually or NC200. Spin down, 300 g for 5 min, re-suspend cells in cold BSS Plus (or BSS/DPBS/HBSS) to generate appropriate dosage for transplantation, Example 5: Reagent and Cell Ware Preparation Complete Medium Preparation (Serum-Free)

Media for culture of human retinal progenitor cells was prepared with the following components:

Advanced DMEM/F12 (Invitrogen),
  Optionally DMEM/F12 (Invitrogen or other brand), or KnockOut DMEM/F12 (Invitrogen or other brand), or neurobasal (Invitrogen), or UltraCULTURE (Lonza), or ReNcell (Chemicon), or other equivalent medium.
N-2 supplement (Invitrogen),
  Optionally B27 (Invitrogen or other brand) xeno-free, or B27 not xeno-free, or Stempro (Invitrogen), or other equivalent.
EGF (recombinant human epidermal growth factor): Invitrogen, optionally other brand
bFGF (basic fibroblast growth factor): Invitrogen, optionally other brand
GlutaMAX I: Invitrogen, optionally L-Glutamine (Invitrogen or other brand)
Gentamicin (Invitrogen) for isolation and first passage (~4-5 days)

Passaging Enzyme:
  Versene solution: Thermo Fisher (Life tech), use as above description at passage 1 and 2. Versene is an EDTA solution for use as a gentle non-enzymatic cell dissociation reagent. Gibco® Versene Solution (0.48 mM) is formulated as 0.2 g EDTA(Na$_4$) per liter of Phosphate Buffered Saline (PBS).

Cryopreservation Medium Preparation

Media for the cryopreservation of cultured human retinal progenitor cells was prepared containing:
  90% Complete medium
  10% DMSO Coating Flasks Human plasma fibronectin (Invitrogen), optionally ornithine, poly-lysine, laminin or Matrigel, dilute in DPBS, concentration: 1-5 µg/cm$^2$, allow 1-3 hours for coating in hood at room temperature, store at 4 C overnight or up to 2 weeks. Rinse with Advanced DMEM/F12 before using.

Example 6: Additional Version of Cell Culture Protocol B

Human retinal progenitor cells were cultured from the retinal cells isolated from the method described in Example 2:

1. Change medium: 100% medium change, change every 2 days. Open systems, closed systems, and semi-closed systems will all work for changing media and passaging cells. Optionally, medium can be changed daily.
2. Passaging: cells are passaged every 4-5 days at 15-95% confluence, optionally 40-95% confluence. Method differs by passage number. Cells can also be passaged every 3-4 days, or every 3-5 days.
   Passage 1: TrypLE Select (Invitrogen)+EDTA (Invitrogen) at 1:4, for 7-8 min at 37° C. incubation.
   Passage 2: TrypLE Select (Invitrogen)+EDTA (Invitrogen)+DPBS (Invitrogen) at 1:1:3, for 5-6 min at 37° C. incubation. T
   Passage 3, and later: TrypLE select (Invitrogen)+DPBS at 1:15-7 min at 37° C. incubation.
   Optionally trypLE Express, trypsin or equivalent, or TRYP-LE EXPRESS or equivalent, 2 fold dilution (equivalent 0.125%) can be used. Dissociation of clusters is stopped by adding DMEM or PBS (10 ml).
3. Dissociation: dissociation of cell clusters is stopped by adding Advanced DMEM or PBS (10 ml). Cell viability and cell number are determined via NC-200. Expected cell viability is >70%. Seed the cells into new fibronectin coated flasks or Cell Stacks (CS) at a density of 1-200×10$^4$/cm$^2$ (early passage 2×10$^6$/cm$^2$, later passage: 1×10$^4$/cm$^2$).
4. Cryopreservation: cells are harvested using TrypLE Select/Express (Invitrogen), optionally trypsin or equivalent, or TRYP-LE EXPRESS or equivalent, at 2 fold dilution (equivalent 0.125%), for 5-7 min, 37° C. incubation. Dissociation stopped by adding DEME or PBS, and then cells were spun down. For a 50 ml tube: centrifuge cells at 490×g for 7 minutes. For a 500 ml conical bottle: centrifuge cells at 700×g for 8 minutes. Re-suspend cells in fresh medium. Cell viability and cell number are determined using an NC200. Add the same amount of 2× cryopreservation medium (20% dimethylsulfoxide (DMSO)) to achieve final 10% DMSO for cell suspension. Aliquot 0.5-10×10$^6$ cells into each cryovial (Themofisher or similar). This is about 10×10$^6$ to about 40×10$^6$ cells per mL of culture medium +10% DMSO. Put the cells into a Cryo 1° C. freezing container (NALGENE) and place the container in a −80° C. freezer overnight (or longer, <2 weeks), then transfer to a liquid nitrogen tank. Alternatively, a Control Rate Freezer can be used to freeze the cells before transferring to liquid nitrogen.
5. Thaw cells: cells are taken out of liquid nitrogen, left in 37° C. water bath for 2-3 minutes until crystals disappear, then transferred into one cold 15 ml conical bottom tube, immediately, using a 1 mL tip. The vial is rinsed with cold fresh medium 1-2 times, 9-12 mL cold fresh medium are then added into the 15 ml tube. Spin down at 1200 rpm (300 g) for 5 minutes. Discard the supernatant, re-suspend the cell pellet in fresh medium, and determine the cell number and viability, as described above for Example 2. Seed cells into new coated flasks or Cell Stacks and incubate under the conditions described above.
6. Prepare cells for transplantation: cells are harvested by TrypLE Express (Invitrogen), optionally trypsin or equivalent, or TRYP-LE EXPRESS or equivalent, 2 fold dilution (equivalent 0.125%), 5-6 min, 37° C. incubation. Dissociation is stopped by adding complete medium, DMEM or PBS. The cell suspension is spun down at 300 g for 5 minutes, and then cells are re-suspended in 0.5-3 ml cold BSS Plus (or BSS/DPBS/HBSS). Cell viability and cell number are determined using Trypan Blue (Invitrogen), counting via Countess (Invitrogen), manually or using an NC200. Spin down the cells at 300 g for 5 minutes, and re-suspend cells in cold BSS Plus (or BSS/DPBS/HBSS) to generate appropriate dosage for transplantation.

Reagent/Cell Ware Preparation:

Complete Medium Preparation (Serum-Free):
  Advanced DMEM/F12 (Invitrogen) was used in this protocol. Optionally, DMEM/F12 (Invitrogen or other brand), KnockOut DEMEM/F12 (Invitrogen or other brand), or neurobasal (Invitrogen), UltraCULTURE (Lonza), ReNcell (Chemicon), or other equivalent medium can be used.

N-2 supplement (Invitrogen), optionally B27 (Invitrogen or other brand) xeno-free, B27 that is not xeno-free, or Stempro (Invitrogen), or other equivalent.

EGF (recombinant human epidermal growth factor): Invitrogen, optionally other brand.

bFGF (basic fibroblast growth factor): Invitrogen, optionally other brand.

GlutaMAX I: Invitrogen, optionally L-Glutamine (Invitrogen or other brand)

Gentamicin (Invitrogen) for isolation and first passage (approximately 4 days, although Gentamicin can be used longer).

Passaging Enzyme:

Versene solution: Thermo Fisher (Life tech), used as in the above description at passages 1 and 2. Versene is an EDTA solution for use as a gentle non-enzymatic cell dissociation reagent. Gibco® Versene Solution (0.48 mM) is formulated as 0.2 g EDTA (Na$_4$) per liter of Phosphate Buffered Saline (PBS).

Cryopreservation Medium Preparation:

90% fresh complete medium.

10% DMSO (dimethyl sulfoxide) (Sigma, optionally other brand).

Coating Flasks:

Human plasma fibronectin (Invitrogen) was used. Optionally, ornithine, poly-lysine, laminin or Matrigel can be used as an alternative.

Dilute fibronectin in DPBS.

Concentration: 1-5 µg/cm$^2$, allow overnight up to 2 weeks coating at 4 C or 1-3 hours for coating in hood at room temperature, store at 4 C overnight or up to 2 weeks.

Rinse with Advanced DMEM/F12 before using.

Flasks can also be used without rinsing with Advanced DMEM/F12.

EQUIVALENTS

The details of one or more embodiments of the invention are set forth in the accompanying description above. Although any methods and materials similar or equivalent to those described herein can be used in the practice or testing of the present invention, exemplary methods and materials are now described.

The foregoing description has been presented only for the purposes of illustration and is not intended to limit the invention to the precise form disclosed, but by the claims appended hereto.

Modifications may be made to the foregoing without departing from the basic aspects of the invention. Although the invention has been described in substantial detail with reference to one or more specific embodiments, those of ordinary skill in the art will recognize that changes may be made to the embodiments specifically disclosed in this application, and yet these modifications and improvements are within the scope and spirit of the invention. The invention illustratively described herein suitably may be practiced in the absence of any element(s) not specifically disclosed herein. Thus, for example, in each instance herein any of the terms "comprising", "consisting essentially of", and "consisting of" may be replaced with either of the other two terms. Thus, the terms and expressions which have been employed are used as terms of description and not of limitation, equivalents of the features shown and described, or portions thereof, are not excluded, and it is recognized that various modifications are possible within the scope of the invention. Embodiments of the invention are set forth in the following claims.

What is claimed is:

1. A method of culturing primary human retinal cells to produce a population of non-immortal human retinal progenitor cells, the method comprising:
   (a) isolating a retinal sample comprising a plurality of primary retinal cells from a human sample, wherein the human sample is one eyeball or a pair of eyeballs, within 8 hours following harvest of human sample from a human donor, wherein the human sample is from a human donor of about 12 weeks to about 28 weeks gestational age,
   (b) dissociating the plurality of primary retinal cells in the retinal sample isolated in step (a) by:
      (i) mechanically dissociating the plurality of primary retinal cells, or
      (ii) enzymatically dissociating the plurality of primary retinal cells by contacting the plurality of primary retinal cells with a protease, wherein the protease does not digest the plurality of primary retinal cells,
   thereby generating a dissociated suspension of primary retinal cells and primary retinal cell clusters comprising at least 30×10$^6$ cells;
   (c) seeding one or more coated culture flasks or plates comprising a culture medium with the dissociated suspension of primary retinal cells and primary retinal cell clusters and culturing for a first passage for about 2 to about 5 days;
   (d) disassociating the first passage by incubating the cells from step (c) with a solution comprising trypsin or equivalent, and ethylenediamine tetraacetic acid (EDTA) at a ratio of 1:4 for 7 to 8 minutes at 37° C.;
   (e) seeding the dissociated cells from step (d) into one or more coated culture flasks or plates containing culture medium and culturing for a second passage for about 2 to about 5 days;
   (f) dissociating the second passage by incubating the cells from step (e) with a solution comprising trypsin or equivalent, EDTA and PBS at a ratio of 1:1:3 for 6 minutes at 37° C.; and
   (g) seeding the dissociated cells from step (f) into one or more coated culture flasks or plates containing culture medium and culture for at least a third passage,
   thereby producing the population of non-immortal human retinal progenitor cells.

2. The method of claim 1, wherein the one eyeball or pair of eyeballs possess a normal morphology comprising intact globe(s), clear cornea, normal shape, or any combination thereof.

3. The method of claim 1, wherein prior to step (a) the human sample is placed in a transport cell culture medium after harvest from the human donor.

4. The method of claim 3, wherein the transport cell culture medium comprises RPMI-1640 with L-glutamine or Advanced DMEM/F12.

5. The method of claim 3, wherein the transport cell culture medium comprises Gentamicin at about 0.5 to 50 micrograms per milliliter.

6. The method of claim 3, wherein the human sample is stored at about 1° C. to 8° C. immediately after placement in the transport cell culture medium.

7. The method of claim 1, wherein step (b) comprises:
   (i) transferring the retinal sample to a tube,
   (ii) mechanically dissociating the retinal sample to produce a plurality of dissociated primary retinal cells, (iii) pelleting the plurality of dissociated primary retinal cells via centrifugation, and
(iv) removing the supernatant.

8. The method of claim 7, wherein the mechanical dissociation of the retina is performed via trituration with a sterile pipet.

9. The method of claim 7, wherein the plurality of dissociated primary retinal cells comprises single cells and clusters of cells.

10. The method of claim 1, wherein the number of viable primary retinal cells is between about $30 \times 10^6$ and about $1 \times 10^9$ viable primary retinal cells, or between about $73\text{-}147 \times 10^6$ viable primary retinal cells.

11. The method of claim 10, wherein the percentage of viable counted cells is between about 10% and about 100%, or between about 68% and about 85%.

12. The method of claim 1, wherein the method further comprises incubating the plurality of dissociated retinal cells at:
(1) 37° C. under 0 to 30% $CO_2$ and 0 to 50% $O_2$,
(2) 37° C., less than or equal to 5% $CO_2$ and less than or equal to 20% $O_2$; or
(3) 37° C., less than or equal to 5% $CO_2$ and less than or equal to 3% $O_2$.

13. The method of claim 1, further comprising a step (h) comprising cryopreserving the plurality of cultured retinal cells.

14. The method of claim 13, wherein the plurality of primary or cultured retinal cells are cultured under conditions comprising:
(1) 37° C. under 0 to 30% $CO_2$ and 0 to 50% $O_2$,
(2) 37° C., less than or equal to 5% $CO_2$ and less than or equal to 20% $O_2$; or
(3) 37° C., less than or equal to 5% $CO_2$ and less than or equal to 3% $O_2$.

15. The method of claim 1, wherein the trypsin equivalent comprises TrypLE.

16. The method of claim 13, wherein cells are seeded in culture flasks or plates at a density of about $0.5 \times 10^6$ to about $3.0 \times 10^6$ cells/cm² at the first passage, about $0.1 \times 10^6$ to about $0.5 \times 10^6$ cells/cm² at the second passage, about $0.03 \times 10^6$ to about $0.2 \times 10^6$ cells/cm² at the third passage, and about 10,000 to about 60,000 cells/cm² at a fourth and further passages.

17. The method of claim 5, wherein the transport cell culture medium comprises about 50 micrograms per milliliter gentamicin.

18. The method of claim 1, wherein:
(a) the one or more coated culture flasks are seeded at a density of about $0.5 \times 10^4$ cells per square centimeter (cm²) to about $5 \times 10^6$ cells per cm²,
(b) the seeding density at the first passage is greater than the seeding density at the second passage, and/or
(c) the seeding density of the second passage is greater than the seeding density of the third passage.

19. The method of claim 18, further comprising one or more further passages, wherein each further passage comprises seeding one or more coated culture flasks or plates comprising or having contained therein culture medium with a plurality of cultured retinal cells produced by an immediate prior passage.

* * * * *